United States Patent
Solomon et al.

(10) Patent No.: US 7,622,137 B2
(45) Date of Patent: *Nov. 24, 2009

(54) DOSAGE FORMS CONTAINED WITHIN A CAPSULE OR SACHET

(75) Inventors: Lawrence Solomon, Boca Raton, FL (US); Allan S. Kaplan, Boca Raton, FL (US)

(73) Assignee: Accu-Break Technologies, Inc., Plantation, FL (US)

( * ) Notice: Subject to any disclaimer, the term of this patent is extended or adjusted under 35 U.S.C. 154(b) by 116 days.

This patent is subject to a terminal disclaimer.

(21) Appl. No.: 11/287,145

(22) Filed: Nov. 23, 2005

(65) Prior Publication Data

US 2006/0165777 A1     Jul. 27, 2006

Related U.S. Application Data

(63) Continuation-in-part of application No. 11/180,930, filed on Jul. 12, 2005, and a continuation-in-part of application No. 11/173,421, filed on Jul. 1, 2005, and a continuation-in-part of application No. 11/173,544, filed on Jul. 1, 2005, and a continuation-in-part of application No. PCT/US2005/018631, filed on May 23, 2005, and a continuation-in-part of application No. PCT/US2005/018633, filed on May 23, 2005, and a continuation-in-part of application No. PCT/US2005/018638, filed on May 23, 2005, and a continuation-in-part of application No. PCT/US2005/018639, filed on May 23, 2005, and a continuation-in-part of application No. PCT/US2005/018632, filed on May 23, 2005.

(60) Provisional application No. 60/584,828, filed on Jul. 1, 2004, provisional application No. 60/573,042, filed on May 21, 2004, provisional application No. 60/573,134, filed on May 21, 2004.

(51) Int. Cl.
A61K 9/20    (2006.01)
A61K 9/22    (2006.01)
A61K 9/24    (2006.01)
A61K 9/44    (2006.01)

(52) U.S. Cl. .............. 424/464; 424/465; 424/467; 424/472; 424/473; 424/468

(58) Field of Classification Search .............. None
See application file for complete search history.

(56) References Cited

U.S. PATENT DOCUMENTS

| 2,633,981 | A | * | 4/1953 | Herrick ............ 206/535 |
| 3,128,226 | A | | 4/1964 | Rubin et al. |
| 4,898,860 | A | * | 2/1990 | Musacchio et al. ....... 514/215 |
| 5,817,340 | A | | 10/1998 | Roche et al. |
| 6,086,919 | A | | 7/2000 | Bauer et al. |
| 6,183,778 | B1 | | 2/2001 | Conte et al. |
| 6,294,200 | B1 | | 9/2001 | Conte et al. |

(Continued)

FOREIGN PATENT DOCUMENTS

JP       H6-9375       *    1/1994

Primary Examiner—S. Tran
(74) Attorney, Agent, or Firm—Ted W. Whitlock

(57) ABSTRACT

Provided are pharmaceutical dosage forms within structures such as hollow capsules, gelcaps, or sachets, adapted to allow ingestion of a whole dose or a preferably predetermined fraction of said dose when desired.

8 Claims, 14 Drawing Sheets

U.S. PATENT DOCUMENTS

| | | |
|---|---|---|
| 6,309,668 B1 | 10/2001 | Bastin et al. |
| 6,544,553 B1 * | 4/2003 | Hsia et al. .................. 424/465 |
| 6,919,373 B1 | 7/2005 | Lam et al. |
| 7,011,849 B2 | 3/2006 | Storm et al. |
| 2002/0132850 A1 * | 9/2002 | Bartholomaeus et al. .... 514/567 |
| 2005/0008690 A1 * | 1/2005 | Miller ........................ 424/451 |
| 2005/0019407 A1 * | 1/2005 | Sowden et al. .............. 424/472 |
| 2005/0038039 A1 | 2/2005 | Fanara et al. |
| 2005/0053648 A1 * | 3/2005 | Chalmers .................... 424/451 |
| 2006/0280794 A1 | 12/2006 | Hamaguchi et al. |

* cited by examiner

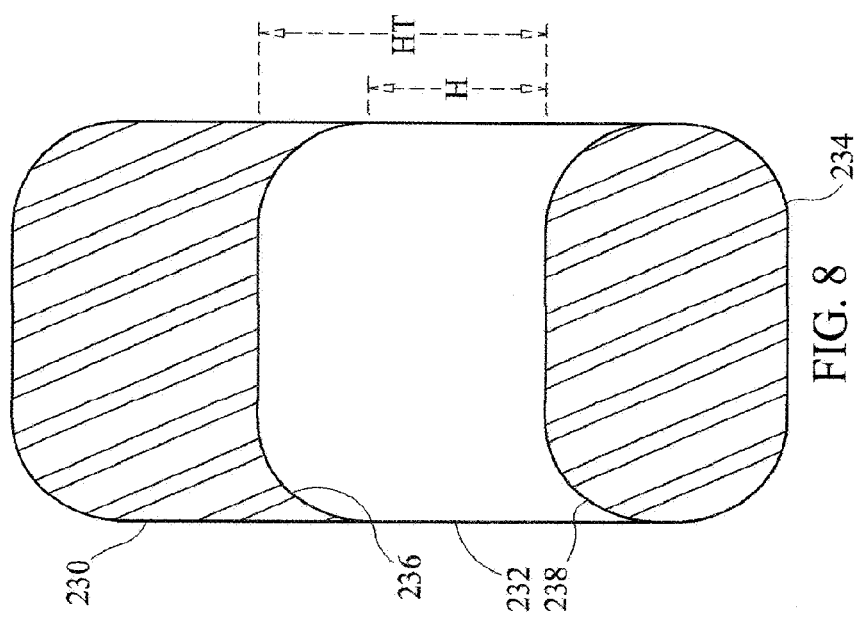
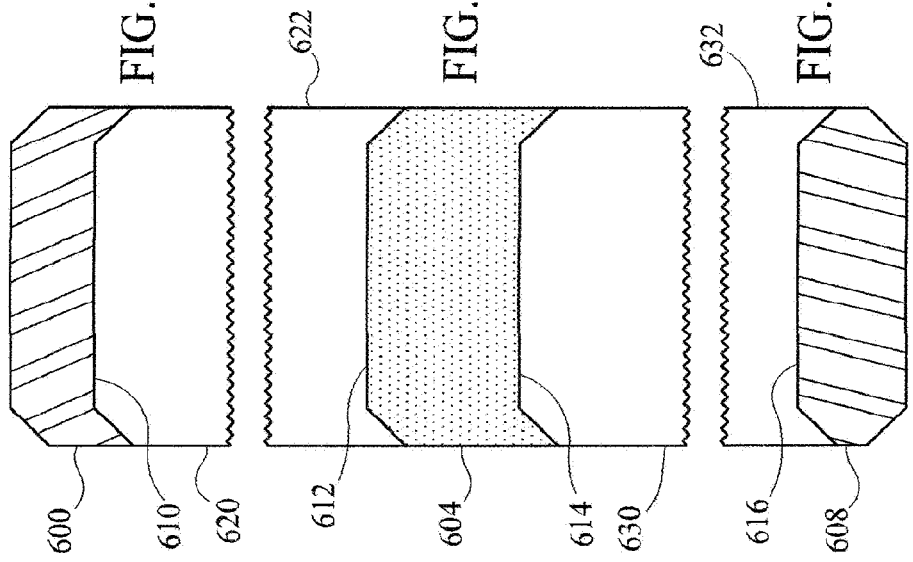

DOSAGE FORMS CONTAINED WITHIN A CAPSULE OR SACHET

CROSS-REFERENCE TO RELATED APPLICATION

This application is continuation-in-part of:

International Applications PCT/US05/18631; PCT/US05/18632; PCT/US05/18633; PCT/US05/18638; and PCT/US05/18639, filed 23 May 2005, each of which designates the United States and claims the benefit of U.S. Provisional Applications, Ser. No. 60/573,042 and Ser. No. 60/573,134, both filed May 21, 2004;

This application is also a continuation-in-part of:

U.S. patent application Ser. No. 11/173,421 filed Jul. 1, 2005, which claims the benefit of U.S. Provisional Application Ser. No. 60/584,828, filed Jul. 1, 2004;

This application is also a continuation-in-part of:

U.S. patent application Ser. No. 11/173,544 filed Jul. 1, 2005; and

This application is also a continuation-in-part of:

U.S. patent application Ser. No. 11/180,930, filed Jul. 12, 2005.

FIELD OF THE INVENTION

The subject invention concerns capsules containing one or more solid dosage forms, novel segmented tablets, or tablets comprising adhesively joined preformed subunits; and related structures, with methods of administration; a preferred object of the invention is to allow administration of an entire dose or, if desired, accurate administration of a portion of said dose.

BACKGROUND OF THE INVENTION

The invention derives from a need to solve at least two related problems within the pharmaceutical industry: (1) inaccurate or inconsistent dose division upon breaking of a dosage form, and (2) inflexibility in adjusting the dose of only one active ingredient in a combination dosage form.

It is well known to provide dosage forms such as tablets or capsules for handling pre-measured quantities of materials that allow consumers to use various materials without the need to use expensive and cumbersome measuring devices. With regard to the first problem of inconsistent or inaccurate dose division, it is known that pharmaceutical tablets are commonly broken to modify the dose provided in a whole tablet. These dosage adjustments through tablet breaking by patients have been determined to be imprecise, whether or not scoring of the tablet is provided.

To aid in breaking, tablets are often produced with a score, which is typically a continuous indentation across a top or bottom surface of the tablet. In addition to top and bottom scoring, it is known to create a vertical score that extends the height of the tablet, created by an "embossing" that is part of the tablet die. For example, Desyrel Dividose®, has a score created by embossing on the top or bottom punch as well as a vertical score running the height (short axis) of the tablet, derived from an "embossing" on a side of the die. However, scoring of pharmaceutical tablets produced in a layered fashion has typically been limited to less than about 1 mm in depth.

Japanese unexamined Patent Application Publication H6-9375 by Ito, et al., (herein, "Ito") discloses tablets that consist of "unit tablets" ("subunits") which are connected by an adhesive "cement". The connecting part is explicitly stated to be the cement, which is described as providing intact subunits by breaking through, either mechanically or by dissolving, said cement connecting part. The Ito application does not disclose producing whole tablets by applying adhesive to an inert subunit which adjoins an active subunit. In addition, Ito does not teach providing a marking or score on or in a subunit to facilitate tablet breaking. The dosage form of the Ito application are broken or divided only through the "cement." Ito further does not disclose placing the structures claimed as novel within a larger structure such as a capsule or sachet.

These previously described attempts have not provided a result which addresses the problem of accurate dividing a dose by splitting of the dosage form. Experts for many years have called upon the pharmaceutical industry to improve the quality of tablet breaking, yet such has not been optimized until the current invention. In 1984, Stimpel et al. ("Stimpel"), described the relative accuracy of breaking various tablets for treatment of cardiovascular problems. M. Stimpel et al., "Breaking Tablets in Half." The Lancet (1984): 1299. Stimpel found that breaking was not accurate, and opined that real world use by patients would provide even more unsatisfactory results.

Rodenhuis et al., (2004) observed that European regulatory authorities, in 1998, started a policy to discourage scoring of tablets. This policy change, likely related to "many recent reports of bad functioning score lines," that "many scored tablets are difficult to break," and that "many scored tablets show unsatisfactory mass uniformity of the subdivided halves." Rodenhuis reported that 31% of all tablets in one Netherlands study were subdivided before being swallowed and noted that "[i]mproving the functioning of score lines may be a more practical approach than banning this [scored] dosage form". N. Rodenhuis et al., "The rationale of scored tablets as dosage form." European J. of Pharmaceutical Sciences 21 (2004):305-308. See also, van Santen, E., Barends, D. M. and Frijlink, H. W. "Breaking of scored tablets: a review." European J. of Pharmaceutics and Biopharmaceutics 53 (2002):139-145.

Peek et al., (2002), studied tablet splitting by elderly patients aged 50-79. Peek, B. T., Al-Achi, A., Coombs, S. J. "Accuracy of Tablet Splitting by Elderly Patients." The Journal of the American Medical Association 288 No. 4 (2002): 139-145. Breaking scored tablets without specific instruction, even with mechanical tablet splitters, led to highly unsatisfactory separating of the tablets. For example, warfarin 5 mg was on average split into 1.9 and 3.1 mg tablets. This potent anticoagulant has such a narrow therapeutic range that 2, 2.5, and 3 mg tablet doses are manufactured. Biron et al., (1999), demonstrated that warfarin 10 mg also often split to less than 4.25 or greater than 5.75 mg. Biron, C., Liczner, P., Hansel, S., Schved, J. F., "Oral Anticoagulant Drugs: Do Not Cut Tablets in Quarters." Thromb Haemost 1201 (1999). In addition, loss of mass due to crumbling or chipping of the breaking of the warfarin tablets was statistically significant. Quartering of the tablets was also grossly inaccurate.

McDevitt et al., (1998), found that 25 mg unscored hydrochlorothiazide ("HCTZ") tablets were manually split badly enough that 12.4% deviated by more than 20% from ideal weight. McDevitt, J. T., Gurst, A. H., Chen, Y. "Accuracy of Tablet Splitting." Pharmacotherapy 18 No. 1(1998):193-197.77% of the test subjects stated they would be willing to pay a premium for individually produced HCTZ 12.5 mg tablets rather than split unscored 25 mg tablets.

Rosenberg et al. studied pharmacist-dispensed split tablets. Rosenberg, J. M., Nathan, J. P., Plakogiannis, F. "Weight Variability of Pharmacist-Dispensed Split Tablets." Journal of American Pharmaceutical Association 42 No. 2 (2002): 200-205. They found that "tablet splitting resulted in an unacceptably high incidence of weight variation" and recommended that "standards should be developed to ensure uniformity of split tablets."

Teng et al., (2002), using a trained individual in a laboratory setting to split tablets, concluded that "the majority of the 11 drug products we tested, when assessed for their ability to be split into half-tablets of equal dose, failed a liberally interpreted USP (United States Pharmacopoeia) uniformity test . . . . The practice of dividing tablets to save costs or to improve a dosage regimen . . . is not recommended for patients using drugs with more substantial toxicity and steep dose-response efficacy curves." Teng, J., Song, C. K., Williams, R. L., Polli, J. E. "Lack of Medication Dose Uniformity in Commonly Split Tablets." Journal of American Pharmaceutical Association 42 No. 2 (2002):195-199.

In the U.S., many managed care insurance organizations recommend or encourage patients to split or divide tablets, including unscored or irregularly-shaped tablets. Many drug products in the US are unscored or are provided as encapsulated powders or pellets despite being able to be produced in tablet form. The dosage forms and methods of the subject invention can advantageously provide a patient with the capability to comply with such recommendations by the managed care insurance organizations A second problem arising relates to combination drug products, which are dosage forms comprising two or more active ingredients. Combination dosage forms are typically produced as homogeneous mixtures or as capsules. A physician prescribing these combination products, such as a combination product currently available to treat arterial hypertension, is not up until now adjust the dose of only one active ingredient in a combination tablet dosage form without a consequent proportional adjustment to the dose of the other active ingredient(s).

Combination dosage forms as are currently taught and practiced therefore have an inherent disadvantage, due to the inflexibility of dealing with changing circumstances such as fluctuating blood pressure or the appearance of side effects to one of the components of the combination. An adjustment to the dose of one of the active ingredients in a commonly available combination product necessarily results in the dose adjustment of the other active ingredient or ingredients contained in that same dosage form. Clearly, dividing a tablet that comprises a homogeneous mixture of a plurality of drugs, or a capsule that contains a homogeneous mixture of two or more active ingredients, divides each of the active ingredients in similar proportions.

Even if the actives of a combination product are layered separately, the layer configuration of currently available combination dosage forms is such that breaking of the tablet results in breaking through all layers, thus dividing all active ingredients proportionally. This disadvantage has been propounded many times over the years, and has hindered the acceptability of certain combination products, for example, in treatments for arterial hypertension ("hypertension"). Nevertheless, even with these disadvantages, combination treatments for hypertension have proven popular for cost and potential compliance reasons. Accordingly, there is a need for combination products which can provide the flexibility of adjusting the dose of one of the actives without necessarily adjusting the dose of the other active(s) contained within the combination dosage form.

Certain combination drug products have been described or marketed having the two or more active ingredients provided in different layers. For example, U.S. Pat. No. 5,738,874 to Conte, et al. describes a multi-layer controlled release tablet having a first layer comprising an immediate release drug composition, a second layer comprising a slow release drug composition, and a third layer comprising a barrier composition to modify release of drug from the layer adjacent thereto. This third, drug-free layer is not interposed between the drug-containing layers and is not useful for facilitating breakage or splitting of the tablet.

Published U.S. Application 2005/0019407A1 describes a composite dosage form which has first and second portions joined at an interface. These dosage forms have a first molded material and a second compressed material. There is no disclosure of any modification of the disclosed dosage forms that would facilitate the breaking of the dosage forms into any subdivided form.

U.S. Pat. No. 6,602,521 describes a multiplex drug delivery system containing at least two immediate release drug dosage packages enveloped by a scored, extended release compartment. There is no teaching from the disclosure of this patent of a controlled release compartment which does not envelop the immediate release compartments.

These prior art dosage forms having an intermediate inactive layer separating active layers are provided only when there is a physical or chemical incompatibility between the different layers containing active drug. In the case of incompatible active layers, the prior art specifically teaches that said "separating layer" be of as limited a size as is necessary to separate the incompatible layers.

There is no dosage form provided in the prior art that adequately addresses these problems facing the industry. The prior art does not describe a dosage form having two layers of active drug or drugs, at least one of which is a controlled release layer, in different places within a tablet with an interposed different layer that can be broken through to accurately and consistently provide modified or divided doses of the active drug or drugs.

Commercially, the only pharmaceutical product to our knowledge that is produced as a taller-than-wide dosage form is Concerta®, which is a layered tablet, having a semi-permeable membrane and utilizes the OROS® system for its controlled release characteristics. The manufacturer's directions for the use of Concerta® specify that the tablets should never be broken. Concerta® does not include a score and does not include an inactive layer interposed between, and therefore physically separating, active controlled release layers. Except for Concerta®, tablets have not been produced that are wider than they are tall, including those involving layers vertically disposed one on the other.

The invention allows several improvements in the art and in the disclosed patent applications listed below. For example, some of the inventions involve layered compressed tablets, or adhesively-joined tablet subunits, adapted for dosage separation when one drug of a combination product is desired to be ingested separately from another component of the combination. Placing such a structure within a capsule that can be opened, or a gelcap that can be cut through or broken, may limit misuse of the novel dosage forms. In addition, placing a thin tablet or deeply scored tablet within a capsule may avoid the limitations for robustness of the physical tablet that can prevent such tablet dosage forms from being commercialized. The latter consideration applies to and explains the need for the novel invention of placing a single, preferably immediate release tablet, within a capsule, whether or not that tablet is a novel segmented dosage form of the above-referenced patent applications.

While a sachet is not considered a dosage form, tablets or capsules of the invention may be placed within a holder such as a sachet to achieve similar purposes as above, although sachets are not heretofore designed to be ingestible.

The present invention, as disclosed herein, can overcome or alleviate both of the problems discussed above, and can provide additional advantages as would be and recognized in the art.

SUMMARY OF THE INVENTION

The present invention concerns a plurality of embodiments for a novel dosage form, and novel methods of use, with the goal of enhancing the flexibility and accuracy of the dosing of pharmaceuticals while maintaining compliance with the basic dosing regimen.

An object of the invention is to provide an encapsulated dosage form that can be used advantageously both as a whole capsule and that can be opened to allow convenient use of only a portion of the contents therein. These contents comprise solid dosage forms and may themselves comprise novel structures as were delineated in pending US patent Applications pending U.S. patent application Ser. Nos. 11/173,421 and 11/173,544 filed Jul. 1, 2005; Ser. No. 11/180,930, filed Jul. 12, 2005; and Int'l Applications PCT/US05/18631; PCT/US05/18632; PCT/US05/18633; PCT/US05/18638 and PCT/US05/18639, filed 23 May 2005; which are hereby incorporated by reference in their entirety.

Another object of the invention consists of the novel methods of use of the inventions as either whole dosage forms or, electively, partial doses.

A preferred dosage form of the invention involves a capsule containing a novel segmented dosage form that generally comprises two or more segments containing a pharmaceutically effective (and generally therapeutically effective, as well) dosage of a drug. The capsule may be ingested whole, or may be opened to allow withdrawal of said tablet, which may then be subdivided to provide the dose desired for ingestion. Benefits of placing said tablet dosage form inside a capsule include inhibiting a patient from subdividing said tablet when not so desired by a prescriber, and protecting the tablet from inadvertent breakage.

Another preferred dosage form of the invention involves a capsule that contains different dosage forms, such as two dosage forms such as tablets or capsules each comprising a therapeutic quantity of a drug.

Another preferred dosage form of the invention involves a capsule that contains immediate release dosage forms such as tablets or capsules that differ in their active ingredients.

Yet another embodiment of the invention involves containers such as sachets that hold or contain the novel dosage forms referred to above, or instead may hold two or more different or similar dosage forms.

In addition, the invention includes a capsule containing exactly one dosage form such as a tablet or a smaller capsule.

Novel methods of administration of the whole or partial doses of the inventions are claimed herein as well, as are novel methods of manufacture.

These and other objects of the invention will become apparent from the present specification.

BRIEF DESCRIPTION OF THE DRAWINGS

FIGS. 7a-c are views of FIG. 5 when the tablet has effectively been broken through two segments in two steps, first by breaking the tablet and then by breaking the tablette of FIG. 6b.

FIG. 8 is a cross-section of a tablet that has three segments.

FIG. 19b is an en face external view of the same tablet shown in FIG. 19a.

FIGS. 23a-23h show cross-sectional representations of embodiments of a capsule or sachet in accordance with the subject invention wherein:

FIG. 23a represents a capsule containing two separate but identical dosage forms;

FIG. 23b represents a capsule containing two separate and non-identical dosage forms;

FIG. 23c represents a capsule containing two separate and non-identical dosage form types, wherein A represents a drug formulated in a tablet dosage form or capsule and B represents a second drug formulated as a powder or pelletized dosage form;

FIG. 23d represents a capsule containing two separate but identical segmented dosage forms having segments comprising a drug A in each of segments A1-A2-A3;

FIG. 23e represents a capsule containing two separate but non-identical segmented dosage forms comprising a drug or drugs A in segments A1-A2-A3 and drug or drugs B in segments B1-B2-B3;

FIG. 23f represents a capsule containing two separate but non-identical segmented dosage forms containing inactive ingredients in segment I between segments A and B, and between segments C and D;

FIG. 23g represents a capsule containing a single segmented dosage form having segments A1-A2-A3.

FIG. 23h shows a hollow capsule containing a single dosage unit.

DETAILED DESCRIPTION OF THE INVENTION

Figure 1B:
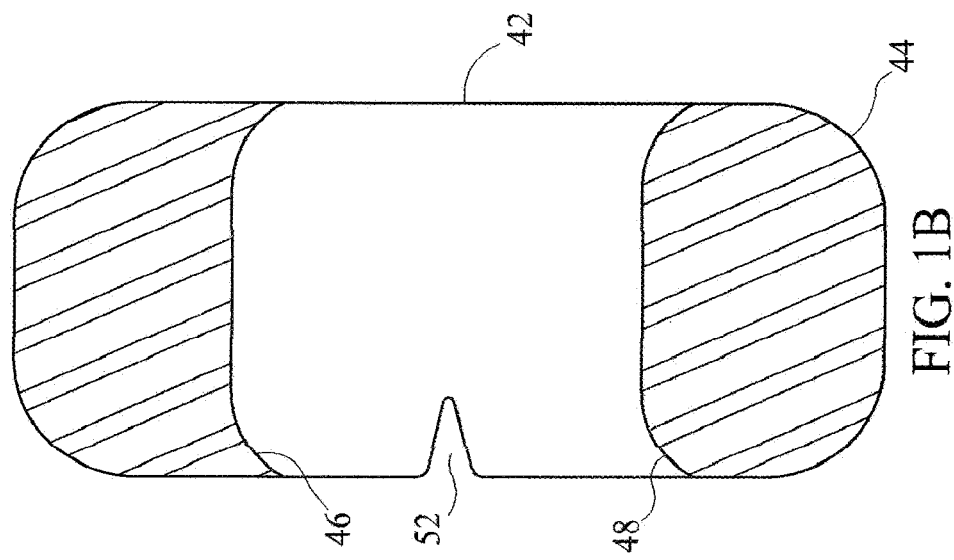
FIG. 1b is a cross-section of the tablet of FIG. 1a looking at the side of the tablet where the score ends.

The subject invention comprises a dosage form adapted for ingestion to provide a whole dose of one or more drugs, or without limitation for accurate subdivision of a whole dose and advantageously providing for administration of the accurately subdivided, or partial dose. The dosage forms of the subject invention are provided within a capsule that optionally can be broken or otherwise opened to expose the dosage form or forms contained therein. Considered as capsules are, for example, conventional hollow structures typically produced from two parts and typically comprise gelatin or all-vegetable material, or gelatin coated tablets, otherwise known as gelcaps. In contrast to a capsule, which may contain such things as liquid, powder, or one or more solid dosage forms, and is intended to be ingestible, a sachet represents packaging that may be a sealed foil pack or a holder to allow dissolution of the contents therein. For convenience, the descriptions below are generally phrased as relating to capsules, but persons of ordinary skill in the art will readily recognize the applicability of the invention to packaging or placement within structures such as sachets.

For purposes of the subject invention, the following terms are also used:

The terms "active agent," "active drug," "drug," "active pharmaceutical ingredient" and "pharmacologically active agent" and the like are interchangeable herein and refer to a chemical material or compound which, when administered to an organism (human or animal) induces a pharmacological effect, and which includes prescription and non-prescription pharmaceutical compounds, and pharmacologically effective amounts of such substances as vitamins and co-factors. Not considered as a "drug" are such substances as foodstuffs or vitamins in "recommended daily allowance" amounts.

A "subunit" is a preformed structure that is adhesively joined to another subunit in a dosage form. Materials such as adhesive substance(s) or film such as hydroxypropyl methylcellulose that may be used to coat a subunit are not themselves considered subunits. Subunits are typically preformed compressed tablets but are not so limited, so that a subunit may for example comprise a capsule.

"Preformed" refers to separate production of a subunit prior to formation of the whole adhesively-joined dosage form. A tablet subunit of a dosage form of the invention is produced as a tablet, and becomes a subunit when it is part of the dosage form of the invention. Similar considerations apply to a capsule subunit of the invention.

A "pharmaceutical dosage form" of the invention herein refers to a solid dosage form. The preferred solid dosage form is an oral dosage form.

An active subunit or an active segment herein contains a pharmacologically effective quantity of a drug or drugs. The terms "drug," "active drug," "active pharmaceutical ingredient" or "active ingredient," "active pharmaceutical compound" and the like herein include not only pharmaceuticals such as those that in the United States are regulated by the Food and Drug Administration, but also includes vitamins and minerals.

In many cases, an inert subunit will adhesively link two discrete active subunits. The term "inert tablet subunit" as used herein means a structural unit made on a tabletting apparatus wherein the structural unit contains pharmaceutically acceptable materials, e.g. excipients, diluents, fillers etc. which have no detectable pharmacological effects at the amounts used in the dosage form. When the term "inactive subunit" or "inactive segment" is used, it is used to describe a subunit or segment which has substantially no detectable pharmacological effects.

When tablets of the invention are broken, the term "tablette" is utilized herein to denote the major fragments arising from said breaking. Breaking a tablet through a bisecting score creates two tablettes, each containing very similar quantities of active ingredients if the tablet is broken through a largely inactive segment of a compressed tablet or an inactive subunit of an adhesively joined dosage form. Small chips and crumbs that typically are formed when a tablet is broken are not considered tablettes.

The invention utilizes the term "segments" in describing the structure of a compressed tablet that comprises different layers.

The dosage forms contained within the capsule can be administered as a whole dose such as by ingestion of the intact whole capsule, but the novel method of use or administration, for purposes of the subject invention, is that they can be separated from one another and administered as a partial dose, or in combination with a second dose or doses not contained within the same capsule.

In a first embodiment, the subject invention comprises at least two separate dosage forms within a single capsule wherein the dosage forms are separately administrable to a patient. For example, two immediate release tablets comprising the same drug, or a plurality of tablet comprising different drugs can be included within a single capsule. The tablets can then be separated following opening of the capsule to provide two doses, one, part of one, or both of which can be administered for treatment as directed. It would be understood that two tablets, each comprising a different active ingredient or drug, can be included within the same capsule so that, if desired, only one of the tablets, and therefore one of the active drugs, is administered.

A further embodiment can include two tablets, each comprising a same combination of drugs, in proportional amounts, so that opening of the capsule can provide a patient with the capability of taking one of the tablets, whereby a reduced dose is administered. For example, a capsule containing two tablets each comprising a combination of amlodipine plus hydrochlorothiazide (amlo+HCTZ) at the same strength can be opened, and the patient can take only one of the amlo+HCTZ tablets, thereby effectively taking exactly 50% of the dose provided in the whole capsule. This can be advantageous over a whole tablet which is broken in order to halve the dose because, as is known, breaking of a whole tablet into two portions can significantly affect or vary the "half" dose that is desired.

Other embodiments contemplated by the invention include, but are not limited to, a capsule containing two tablets each comprising the same active drug or drugs at various strengths; two tablets each comprising the same active drug or drugs formulated to release drug at various rates from the composition; a first tablet comprising a first drug and a second tablet comprising a second drug (which second tablet can also include the first drug); three or more tablets each comprising one or more active drugs; at least one tablet comprising at least one active drug and a second dosage form, e.g., a capsule, caplet, powder or pellet formulation comprising an active drug whereby a tablet dosage form is readily separable from the other dosage form so that it can be administered separately from the other dosage form contained within the capsule. Other variations and all permutations of the above configurations would be readily apparent to persons of ordinary skill in the art and are intended to be included within the scope of the subject invention.

In a preferred embodiment of the subject invention, the capsule contains a dosage form comprising a vertically disposed layered, compressed tablet. The vertically disposed layered tablet can be configured as a taller-than-wide segmented tablet, as disclosed and described in Int'l Application PCT/US05/18633 which is incorporated herein by reference. Preferably, these tablets can include a relatively inactive layer for breaking therethrough in order to avoid breaking through of a portion of the tablet, e.g., a segment, which includes active drug ingredient. Such tablets comprising an inactive layer or segment are disclosed and described in various applications which are incorporated herein by reference, including but not limited to PCT/US05/18639.

In another embodiment, the invention provides a pharmaceutical tablet comprising unitary segments. Unitary segment compositions are disclosed and described in Int'l Applications PCT/US05/18631 and PCT/US05/18632 which are incorporated herein by reference.

The capsule of the subject invention can also contain a pharmaceutical dosage form comprising a plurality of adhesively-joined subunits (which themselves may be segmented subunits). Said dosage form in a preferred form contains at least one or more of the following:

(a) a first inert tablet subunit and a second active subunit; or (b) a first tablet subunit with a pharmacologically inactive layer in which said layer has a mass of at least 20 mg and a second subunit; or (c) a separation mark on a tablet subunit; or (d) a first tablet subunit and a second capsule subunit.

The dosage forms of the invention may include tablets or capsules which are shaped in any desired configuration by such means as the use of tablet punches and dies (tablets), or encapsulating equipment (capsules).

The dosage forms of the subject invention may comprise active subunits and inert tablet subunits having a plurality of various cross-sectional shapes, including without limitation round tablets, half-round, quarter-round, oval, trapezoidal, triangular, rectangular, etc., that are be adhesively bonded to each other.

These adhesively joined dosage forms can be manufactured by:

(a) applying adhesive to a first active or first inert subunit; and (b) bringing said first active or inert subunit containing adhesive into contact with a second active or inert tablet subunit (that optionally may have adhesive applied as well) and optionally applying pressure to the subunits.

Adhesively joined tablets according to the subject invention are disclosed and described in U.S. patent application Ser. No. 11/173,421, which is hereby incorporated by reference.

Each of the novel dosage forms can be provided in many embodiments and may comprise many different arrangements, shapes, types of active ingredient(s), types of inactive ingredient(s), number of subunits, etc. without any limitation. Examples representing embodiments of the invention are given herein to exemplify but not to limit the number of useful possibilities that are within the scope of the invention.

Preferred embodiments of the subject invention advantageously allow precise division of a tablet dosage form contained within a capsule by allowing tablet breaking to occur, when desired, only through a single layer or segment so that maximal accuracy of dosing with a tablet fragment arising from intentional tablet breaking may occur. In a preferred use, the segment to be broken through lacks an active drug (i.e., it is an inactive granulation).

Tablet dosage forms of the subject invention may also include a separation mark that without limitation comprises a score, indicia, a gelatin band, or color delineation. Tablets comprising a separation mark are disclosed and described, for example in Int'l Applications PCT/US05/18632 and PCT/US05/18638, which are incorporated herein by reference.

One method of making a scored tablet of the invention utilizes a lower punch of a tablet die that includes a protuberance known as an embossing. An embossing can preferably bisect or quadrisect said lower punch, so that compression causes the first layer to be divided into two or more non-contiguous segments. A layer formed into two or more non-contiguous segments is herein referred to as a divided layer; said segments formed from a divided layer are herein referred to as unitary segments.

Tablets with layers of different colors have not before been configured or utilized so that a layered tablet may be broken through one layer rather than all layers. The tablet of the subject invention can, for example, have a first lower and a second upper segment having the same color and contain either the same drug in a pharmacologically effective quantity or both lack a pharmacologically effective quantity of any drug, and a third inner, interposed segment that has a different color from said first segment and has either the same drug as said first segment when said first segment has a pharmacologically effective quantity of a drug or has no pharmacologically effective quantity of a drug when said first segment lacks a pharmacologically effective quantity of any drug.

In use, a capsule containing layered or segmented tablets as described, can be opened by separating interconnecting sections of the capsule, for example, by applying a twisting and pulling motion to the capsule sections, to separate the sections and thereby expose the contained dosage forms. Alternatively, the capsule can be cut or sliced open using a cutting edge or appropriately adapted implement in order to split the capsule, preferably without also cutting into the dosage forms contained within the capsule. Once opened, the exposed dosage form(s) can then be separated from each other (if there are a plurality of dosage forms) and/or broken as appropriate, and then ingested to administer the desired dose, e.g., a half dose of a whole active drug or a therapeutic dose of a first drug and none of a second drug that was also present within the capsule.

In a preferred embodiment of the invention, a single dosage form from within the capsule can be separated from another dosage form that may be provided within the capsule. If the single dosage unit is further breakable, e.g., comprising a segmented configuration providing a divisible dose in accordance with certain embodiments described herein, that divisible dosage form can be further accurately broken with regard to the active drug(s) contained therein. Preferably, a divisible dosage form such as a segmented tablet is conveniently breakable into tablettes without damaging the function or dosage quantity of any or segment. Such non-damaging separation of at least one active or formation of a tablette may be performed manually, but mechanical breaking means such as utilizing a knife, razor blade, or commercially available tablet splitter are suitable, as well.

Following separation of one dosage form from another from a capsule, or breakage of a tablet contained within a capsule to form tablettes, the desired dosage form(s) or tablette(s) can be administered to or taken by the patient as directed.

Another embodiment of the invention involves a hollow capsule that contains within it a single solid dosage form such as a tablet or smaller capsule, said dosage form not being limited to any of the novel dosage forms referenced in the patent applications above.

Examples of specific embodiments of the invention can be understood with reference to the drawings. The drawings depict vertical cross-sectional views of tablets and tablettes of the invention. Tablets are depicted as if they were in the die, so that the top of the tablet as it is oriented on the page corresponds with the top of the tablet in the die. In other words, the top segment of the tablet as viewed contains the last granulation to enter the die. Tablettes are depicted as they would have been in the die before they were separated from the intact tablet. Shaded areas represent segments derived from active granulations, i.e., those which contain a drug; clear (plain) areas represent segments derived from inactive granulations, i.e., those formulated with no active drug. Drawings of capsules containing one or more dosage forms also represent vertical cross sections as if the capsule were "standing on end."

Figure 2C:
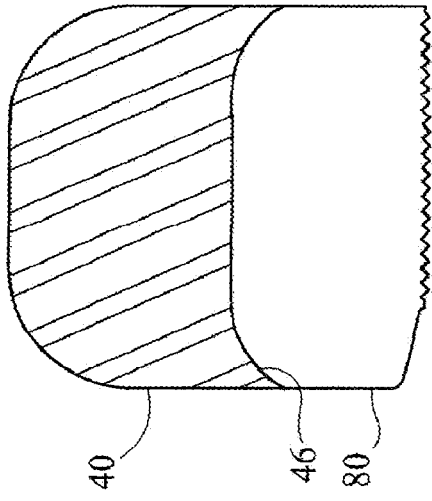
FIGS. 2a-b and 2c-d are views of FIG. 1a and FIG. 1b respectively when the tablets have been broken through the score.
Figure 2D:
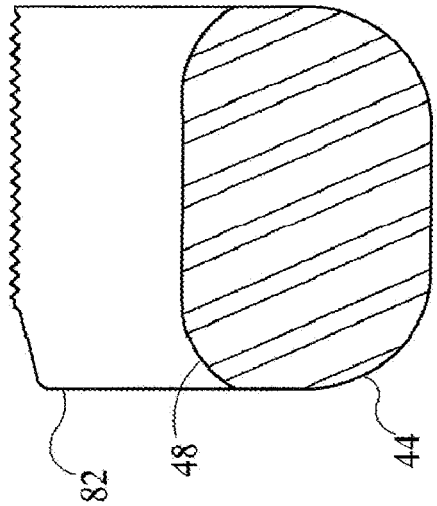

"Front views" refer to a cross-sectional view of a tablet that has a theoretical geometric plane passed through the tablet relative to a side which is arbitrarily designated as the front. Figures labeled as "side view", which also have a corresponding "front view", are taken as a cross-section through the whole tablet from the right side of a front view i.e. a side view is a cross-section that is taken by passing a plane through the vertical axis of the whole tablet at a 90° angle to the cross-sectional front view. Each front view represents a schematic cross-section that passes through the midpoint of the horizontal cross-section as measured from the front of the tablet to the back of the tablet or tablette. The front view is also parallel to the major axis of the tablet (e.g., for a tablet with a rectangular (but not square) transverse cross-section, the longer side of the perimeter is parallel with the plane that depicts the cross-sectional, front view). That plane is located half-way between the front and back surfaces of said tablet. The side views of FIGS. 1b and 2c-d are taken from a vertically-oriented plane that passes through the midpoint of the longer transverse dimension (i.e., the width), and thus are located at and perpendicular to the mid-point of the front view. Drawings are of tablets that have a rectangular but not square horizontal cross-section at the vertical mid-point of the tablet.

Segments containing pharmacologically active amounts of a drug or drugs are shown crosshatched; pharmacologically ineffective segments are shown plain (clear, without crosshatching or stippling). For consistency, tablettes are depicted in the same orientation as the tablets from which they are formed, although tablettes are created after tablet ejection from the die. Dotted lines in the tablets depicted in the figures may represent printed marks or other indicia, or scores that are present on or in the surface of the tablet and, if they represent a score, said score does not extend deeply enough into the tablet to appear in the cross-sectional front view. The transverse dotted lines reflecting scores shown in the Figures imply no intention to limit the depth of any scores of the tablets of the invention. Horizontal dotted lines on the front views that represent the surface scores are schematic, and do not necessarily represent the full vertical extent of a score, printed mark, or the like.

Tablettes are depicted with broken surfaces as indicated by a saw-tooth pattern. Such saw-tooth depiction is schematic and not intended to represent the actual pattern of breaking of a tablet (or tablette), which often leads to irregular edges even if said tablet is broken through a score.

Separation marks in the tablets depicted in the Figures are depicted as scores that are present on or in the surface of the tablet and that do not extend deeply enough into the tablet to appear in the cross-sectional front views are depicted in the drawings as dotted lines to reflect the location of said scores on or in the surface of the tablet (not shown). It is to be understood that the depth of a separation mark or other score may be deeper than one-half the widest cross-section of the tablet in a particular embodiment, and thus the transverse dotted lines reflecting scores that are separation marks shown in the Figures imply no intention to limit the depth of any scores of the tablets of the invention. Similarly, the tablets shown that contain scores do not limit the width or extent of said scores. The horizontal dotted lines on the front views that represent the surface scores are schematic, and do not necessarily represent the full vertical extent of the score. (Perforations or discontinuous scores through the width or depth of the tablets are not depicted herein, but remain within the scope of the invention, as are other marks on or physical changes to the tablet that create a separation mark.) Any scores or printed indicia that serve as separation marks are for convenience herein assumed to be on the front surface of the tablet, which is arbitrarily chosen from a vertically-oriented surface of the tablets. The "side view" of a tablet is a cross-sectional view of the tablet rotated 90 degrees from the front view, and is shown in FIGS. 2c and 2d. No dimension of the separation marks is limited by their depiction as dotted lines in any figure.

The Figures that are discussed below include descriptions of tablets that are, according to the invention intended to be placed within hollow capsules, coated with a substance such as gelatin to create a gelcap or, as discussed below and elsewhere herein, such structures as sachets.

Figure 1A:
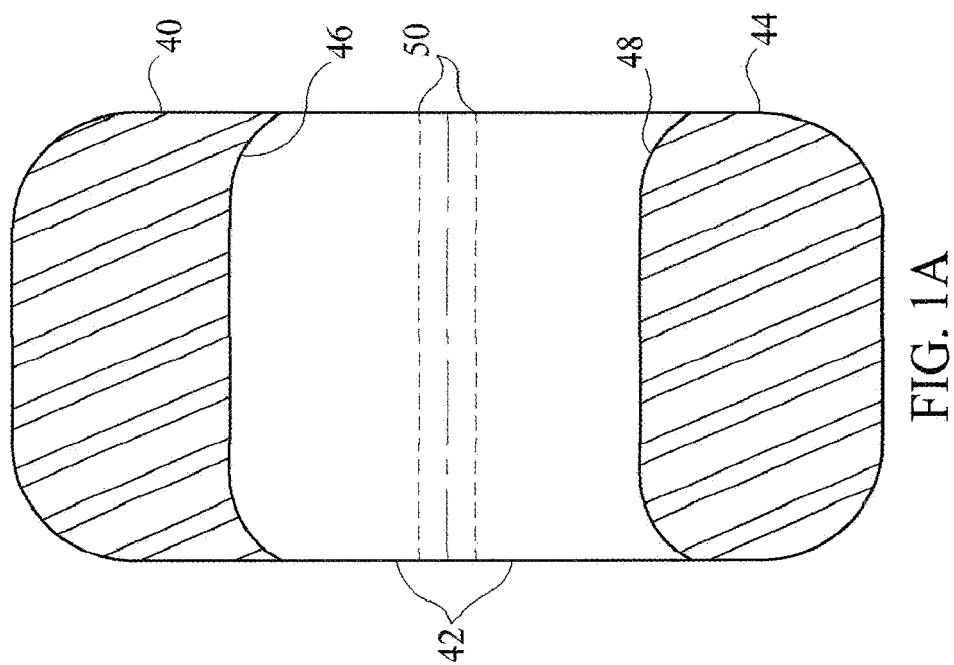
FIG. 1a is a cross-section of a taller than wide tablet looking towards the side of the tablet that has a score.

FIGS. 1a and 1b depict a tablet with compositionally substantially identical upper segment 40 and lower segment 44. In a preferred embodiment, a controlled-release formulation of a metoprolol salt is present in each segment. Inner segment 42 contains trace amounts of the drug that is present in a therapeutically effective quantity in each of segments 40 and 44; in a preferred embodiment said drug comprises coated particles of metoprolol. Interfaces 46 and 48 represent regions in which the upper part of segment 42 and the lower part of segment 42 respectively adjoin upper segment 40 and lower segment 44. The curved interfaces result from the profile of the upper tablet punch which is curved. Score 52 is depicted in FIG. 1b. Dotted line 50 in FIG. 1a is a reflection of score 52 on the surface of the tablet (not shown), that does not penetrate half-way through the shorter transverse axis of the tablet.

FIGS. 2a-d depict tablettes formed from breaking the tablet of FIGS. 1a and 1b through score 52. Inner segment 42 of FIG. 1a no longer exists as an intact segment. The upper tablette of FIGS. 1a and 1c contains segment 80 that adjoins intact upper segment 40 and the lower tablette contains segment 82 and intact segment 44. Because of the taller-than-wide configuration, breaking the tablet of FIGS. 1a and 1b through the score placed in segment 42 is easier than breaking the tablet through its vertical dimension, which is currently the practice with scored layered (segmented) tablets, though it should be noted that the current and limited practice of scored layered tablets involves, probably exclusively, tablets that are taller than they are wide. The fact that during preferred means of breaking said tablet, no break is made in the parts of the tablet where the active drug has been placed provides for exceptionally accurate breaking relative to the active drug or drugs contained in the tablet.

Figure 3:
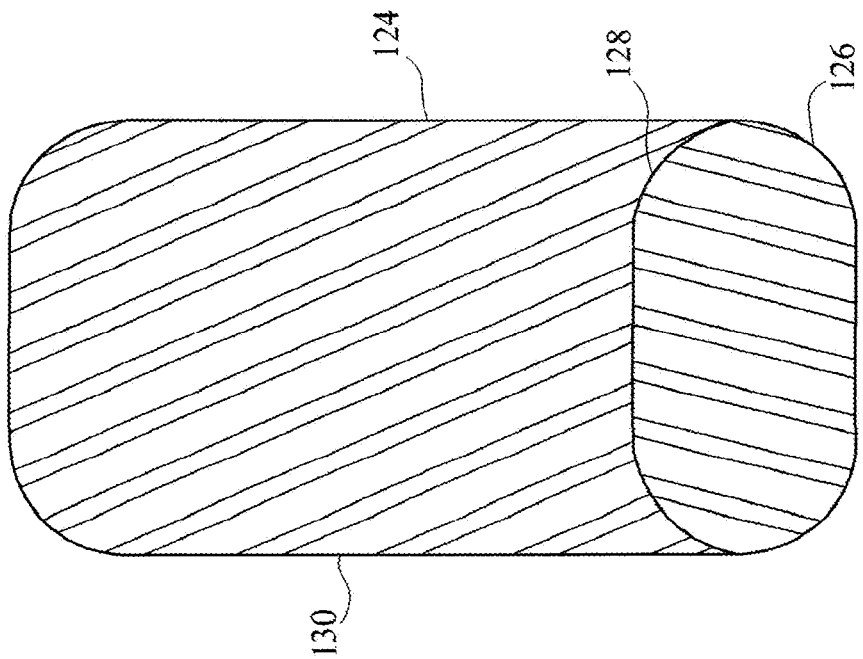
FIG. 3 is a cross-section of a taller than wide tablet having two segments, one of which is about three-quarters of the height of the tablet.

FIG. 3 demonstrates a two-segment tablet, each segment formed from a granulation containing a pharmacologically effective amount of medication. In a preferred embodiment, coated particles of verapamil that create a controlled release of said drug comprise upper segment 124 and an immediate release granulation of verapamil comprises lower segment 126. Upper (outer) segment 124 is larger than lower (outer) segment 126. Interface 128 indicates a region (interface) at which said segments are contiguous. A printed mark on the outer surface of the tablet (not shown) indicates a potential breaking point, as indicated by the location of arrow 130 that reflects the position of said surface printed mark. The two segments 124 and 126 also have different colors; however, further allowing identification of which part of the tablet contains which segment.

Figure 4A:
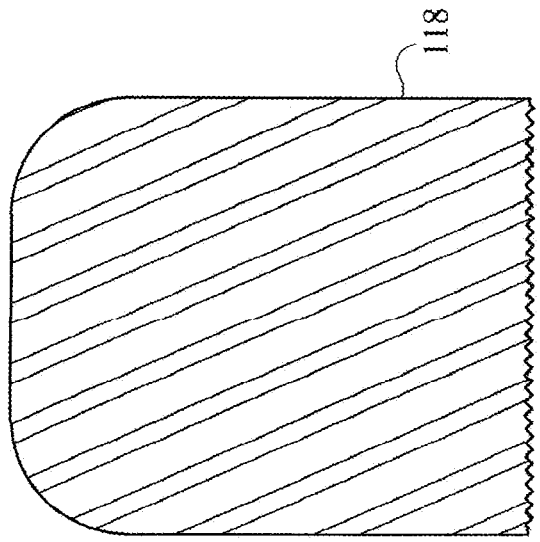
FIGS. 4a-b are views of FIG. 3 when the tablet has been broken transversely.
Figure 4B:
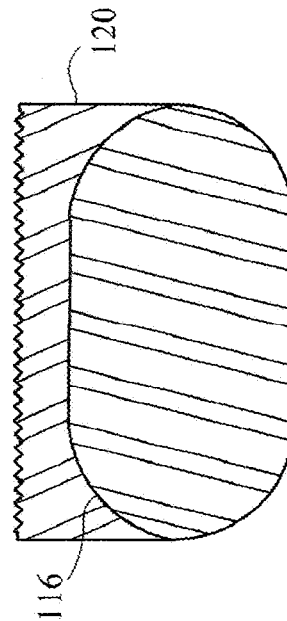

FIGS. 4a and 4b depict the two tablettes formed by breaking the tablet of FIG. 3 though not as directed by print mark as indicated by arrow 130. The tablette of FIG. 4a consists of segment 118, which represents the bulk of segment 124 of FIG. 3. The tablette depicted in FIG. 4b contains segment 112 in an intact form and segment 120, which represents a less than half-portion of segment 124 of FIG. 3. Interface 116 indicates a region at which said segments are contiguous. The curvature of interface 116 is due to the profile of the upper tablet punch.

Figures 6A, 6B:
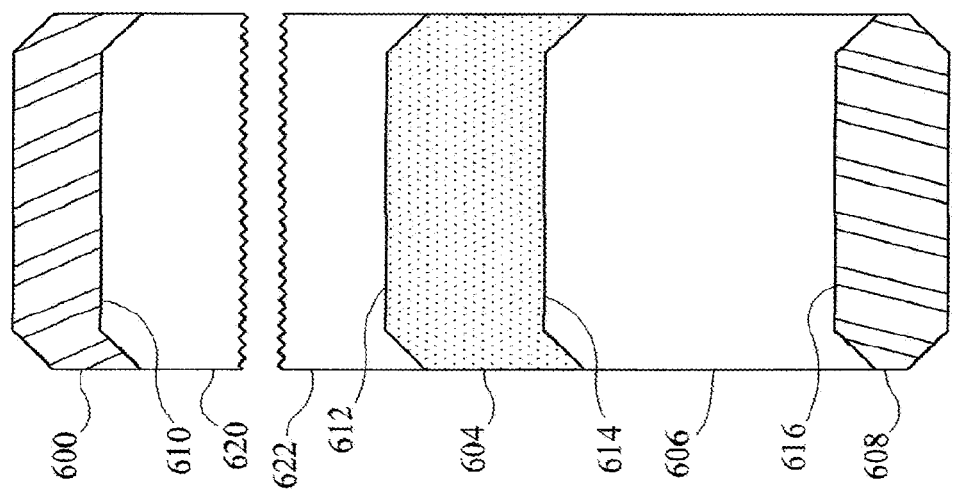
FIGS. 6a-b are views of FIG. 5 when the tablet has been broken through one segment.
Figure 5:
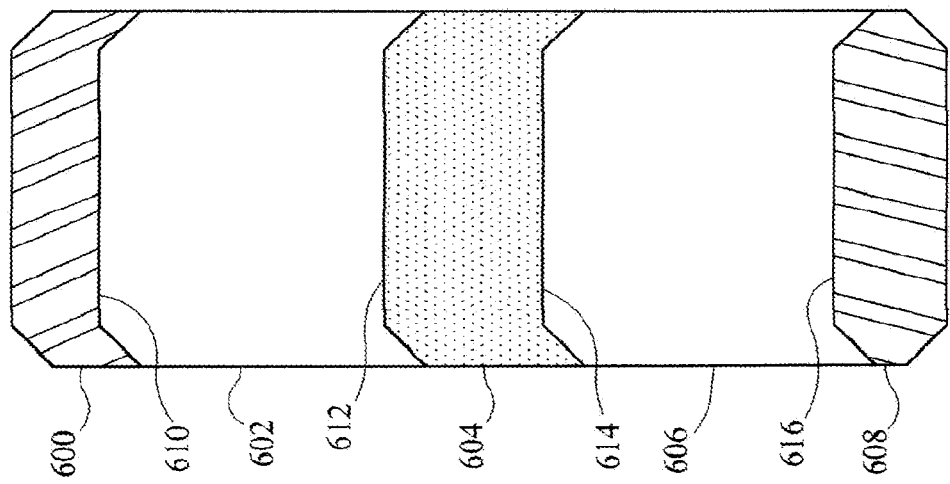
FIG. 5 is a cross-section of a taller than wide tablet having five segments.

FIG. 5 illustrates a tablet more elongated than those previously demonstrated. Said tablet is adapted, even more than the others, for ease of breaking through one segment. Upper segment 600 is provided with a therapeutic quantity of a drug; stippled inner segment 604 is provided with a therapeutic quantity of a different drug; and, lower segment 608 is provided with a therapeutic quantity of a drug different from that found in a therapeutic quantity in segments 600 and 604. Clear (plain) inner segments 602 and 606 contain pharmacologically ineffective amounts of each of the three drugs found in the tablet, though in less preferred embodiments, inadvertent mixing of the three different granulations is sufficient to produce a pharmacologically effective though not therapeutically effective dose of a drug or drugs. In yet a different embodiment, segment 604 is provided with a therapeutic quantity of a vitamin such as folic acid; and in addition, in a less preferred embodiment, segment 606 may also be provided with a therapeutic quantity of a drug as well. Interfaces 610, 612, 614, and 616 represent the regions at which two contiguous segments adjoin. The tablet of FIG. 5 is provided with a different color for each segment, though no requirement for this color differentiation by segment exists for tablets of the invention. Even though there is no surface scoring or indicia, the color scheme is such that a person's attention may be directed to apply force to break the tablet through segment 602 to create the tablettes depicted in FIGS. 6a and 6b. FIG. 6a depicts the smaller tablette created by breaking the tablet of FIG. 5 through segment 602 in a transverse fashion. Segment 620 has been created by said breaking, and segment 602 of FIG. 5 no longer exists as an intact segment. FIG. 6b depicts the larger tablette created by said breaking of the tablet of FIG. 5. New upper segment 622 has been created.

Segment 608 of the tablet of FIG. 5 comprises an altered-release pharmaceutical agent chosen from those well known in the art. No limitation of the ratios of the five segments of said tablet relative to the dimensions of the whole tablet exists.

FIGS. 7a-c depict three tablettes created by the subsequent breaking of the tablette of FIG. 6b. New segment 630 and segment 632 have been created and segment 606 no longer exists as an intact segment. Assuming minimal to no intermixing between the materials forming each segment of the tablet of FIG. 5 and assuming that segment 632 of FIG. 7c is substantially free of any active drug, the tablette of FIG. 7c represents a novel altered release dosage form, in part in that it consists of an altered release product adjoining in a segment an immediate release substantially inactive segment.

FIG. 8 is a cross-section view of a tablet with three segments. As FIG. 8 demonstrates, cupping or beveling of the upper punch commonly causes the peripheral parts of any segment other than the lowest segment, to extend below the level of the central part of that segment. In order to fully realize the benefit of a "separating segment" per the invention, it is optimal that a transverse plane be able to be placed between the lowest part of a superiorly disposed segment, and the highest part of an inferiorly disposed segment, with said plane passing between an interposed, preferably pharmacologically inactive segment. The vertical distance between the lowest part of a superiorly disposed segment and the highest part of an inferiorly disposed segment is herein denoted the effective height H, which is less than the height HT of the middle segment in FIG. 8 due to cupping of the upper punch. Generally, that measurement will be from the vertical height from the bottom of the tablet to the plane drawn horizontally from the periphery of the higher segment, due to the cupping or beveling of such a segment, and from the vertical height from the bottom of the tablet to the center of the lower segment.

The effective height in the case of beveling or cupping of segments, as easily reflected in the shape of the top of the tablet, is always less than the height of the separating or interposed segment through which breaking is intended to occur. The height of an interposed segment is the vertical distance from its highest point to the highest point of the contiguous superiorly disposed segment.

Figure 9:
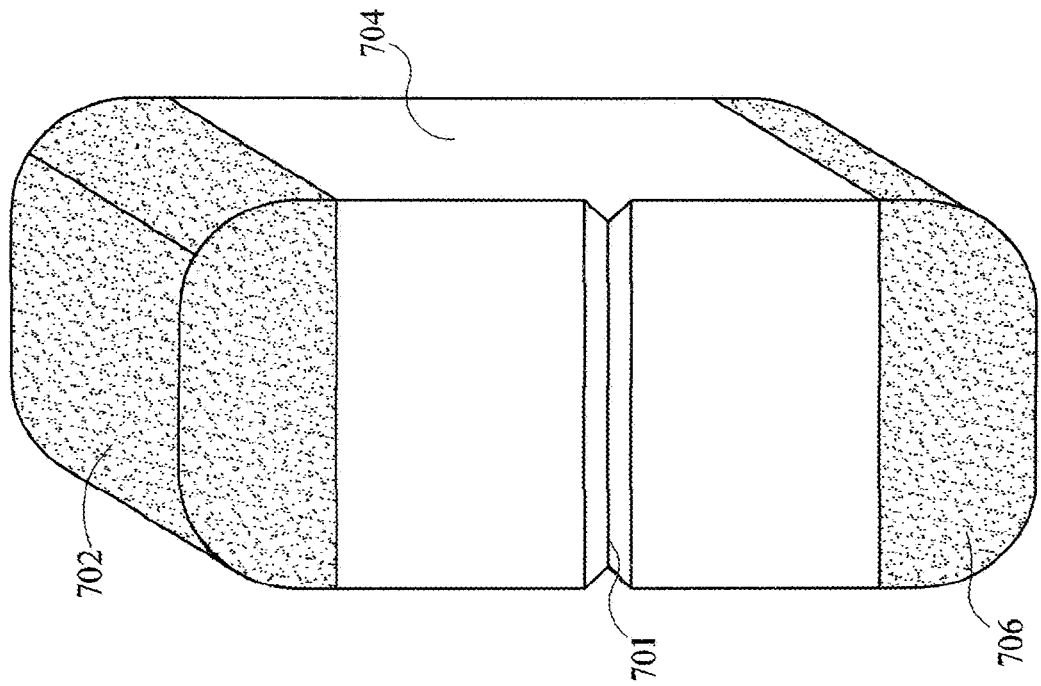
FIG. 9 is an external perspective view of a scored tablet that has three segments.

FIG. 9 is a perspective view of a tablet of the invention which shows score 701 as a separating mark on a front surface and top active (drug-containing) segment 702; middle pharmacologically inactive segment 704 (no pharmacologically effective amount of a drug) and bottom active segment 706. When the tablet is broken through the score 701, the top segment and the bottom segment will remain intact. Segments 702 and 706 each contain a compositionally identical controlled release beaded formulation of verapamil plus immediate-release hydrochlorothiazide ("HCTZ"). Pharmaceutically ineffective quantities of verapamil and HCTZ are found in segment 704.

Figure 10:
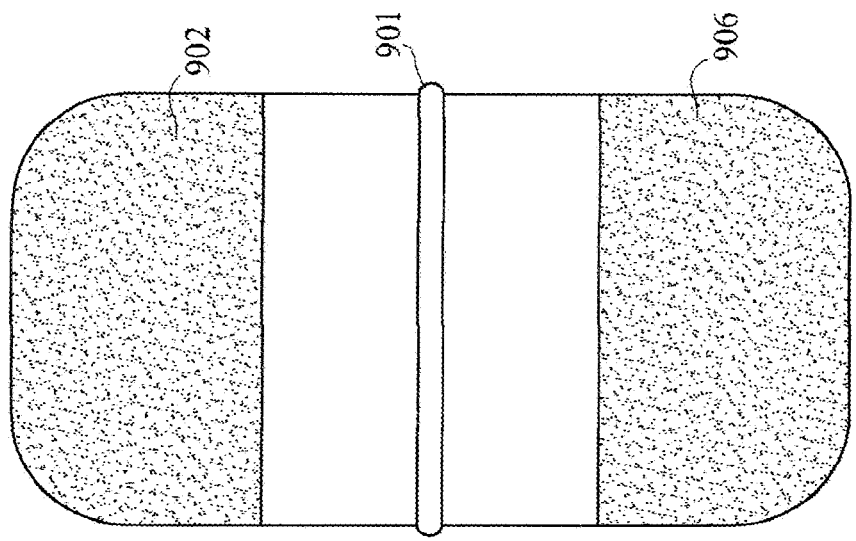
FIG. 10 is an external en face view of a tablet that has three segments and that has a band around the width of the middle (inner) segment of the tablet that extends to the sides.

FIG. 10 is a front view of a tablet of the invention showing a gelatin band 901. Techniques such as those used to band capsules, as disclosed in U.S. Pat. No. 4,922,682, which is incorporated by reference, may be modified to provide a band in making tablets according to the invention. Segments 902 and 906 are compositionally distinct and contain different volumes of material. Lower segment 906 comprises potassium chloride in a matrix formulation; upper segment 902 comprises an immediate-release composition of chlorthalidone. Middle (inner) segment 903 contains small amounts of chlorthalidone but not in a pharmaceutically effective quantity.

Figure 11:
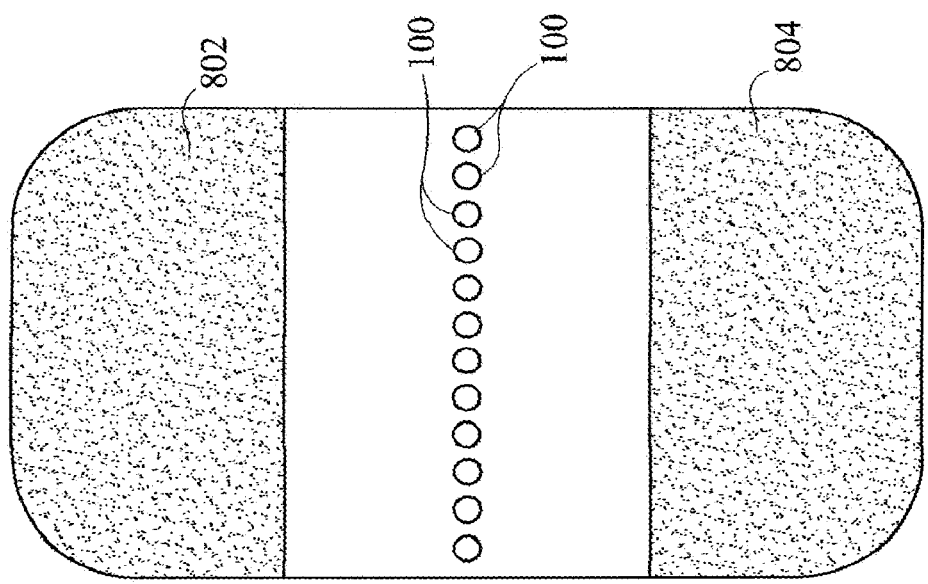
FIG. 11 is an external en face view of a tablet that has three segments into which perforations have been created in the middle segment.

FIG. 11 shows a series of perforations 100 that may be made in the surface of a tablet to form a separation mark according to the invention. These perforations may be formed e.g. by mechanical or laser drilling 1-2 mm diameter holes that extend into the surface to a depth of 1-2 mm. The stippled upper and lower segments 802 and 804 contain a modified release preparation of pentoxyphylline. Un-numbered middle segment containing perforations 100 comprises inactive excipients.

Figure 12:
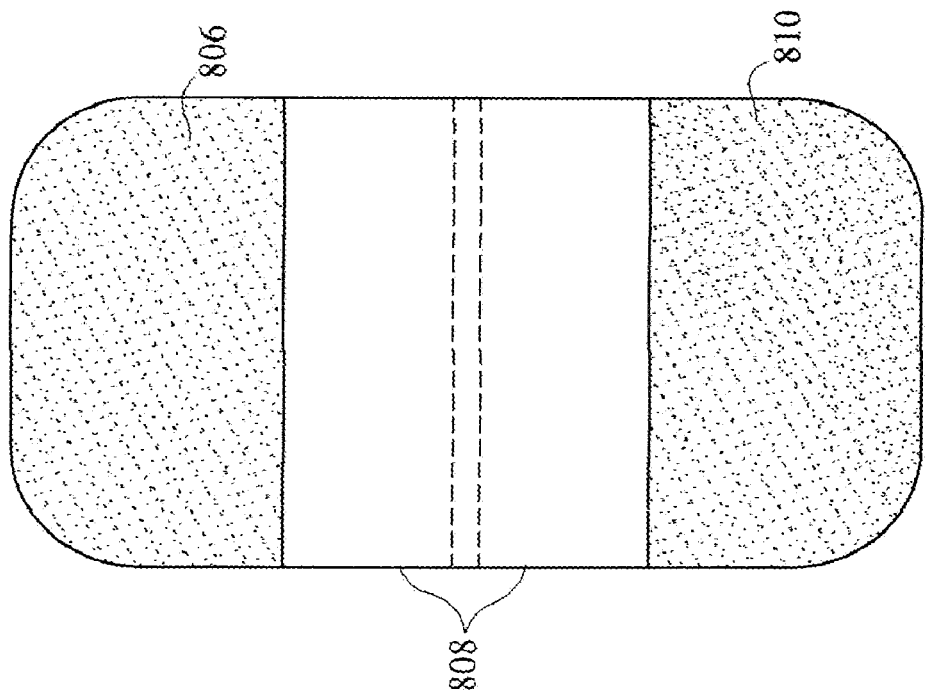
FIG. 12 is an external view of a tablet with three segments on the middle segment of which are two horizontal (transverse) dotted lines close together.

FIG. 12 shows a front view of a tablet according to the invention that has two printed dotted lines that serve as a separation mark according to the invention. Middle segment 808 comprises a therapeutically effective quantity of folic acid and vitamin B12. Lower segment 810 comprises controlled release beads of a metoprolol salt in a therapeutic quantity and upper segment 806 comprises a therapeutic quantity of amlodipine. Sub-therapeutic quantities of the following drugs are found in the following segments: folic acid and vitamin B12 in segments 806 and 810, metoprolol in segments 806 and 808, and amlodipine in 808 and 810.

Figure 13:
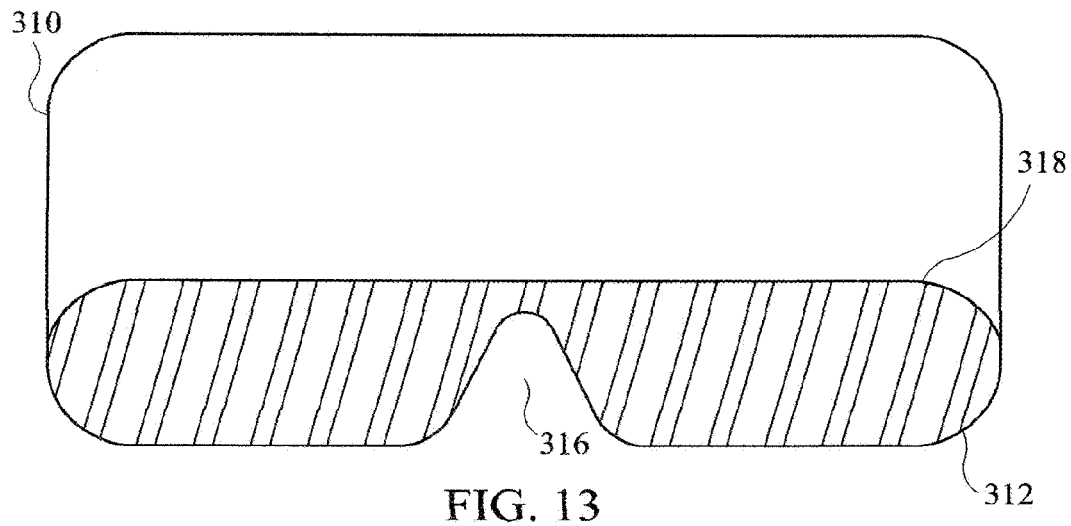
FIG. 13 is a cross-section of a wider than tall tablet with two segments one of which is deeply scored.

FIG. 13 depicts an immediate release tablet with a score 316 that extends approximately 90% through the bottom segment 312. Upper segment 310 allows structural stability of the tablet despite the deep score 316. In this tablet, no pharmacologically effective dose of the drug present in segment 312 is present in segment 310. In another preferred embodiment, segment 310 may contain a different drug than is present in segment 312, preferably in a pharmacologically effective quantity. In a less preferred embodiment, segment 310 contains a pharmacologically effective quantity of the drug or drugs present in segment 312, but in a diminished concentration relative to the excipients in each segment. Interface 318 is present. In this tablet, an active drug in a composition with altered release characteristics is present in a therapeutic quantity in segment 312, and segment 310 lacks a therapeutic quantity of the same or any other drug. The novelty of the tablet design would remain, however, were segment 310 to be provided with drugs such as a pharmaceutically effective or therapeutically effective quantity of a different drug. Novelty would also be present, for example, if the altered release composition were present in a therapeutically effective quantity in unscored segment 310 and a therapeutically effective quantity of a different immediate release composition of a drug were present in scored segment 316.

Figure 2A:
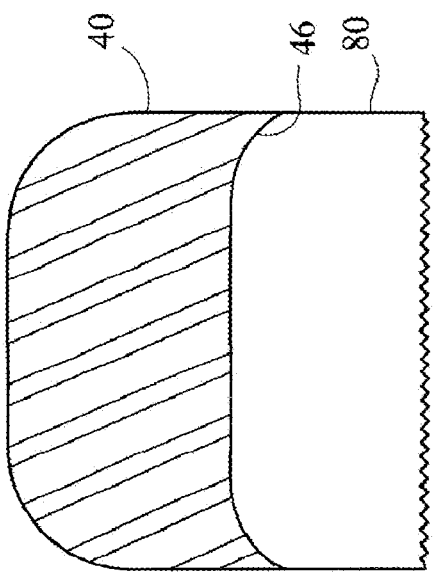
Figure 2B:
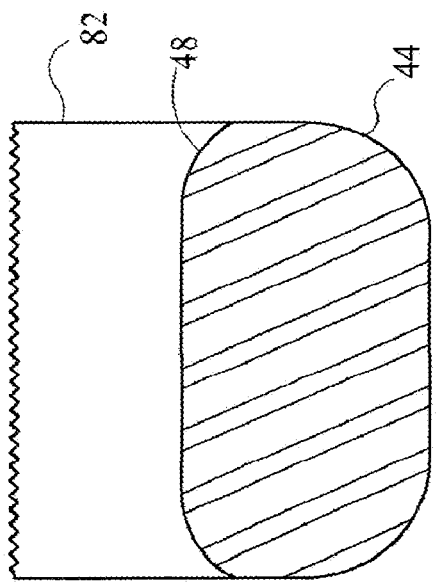
Figures 14A, 14B:
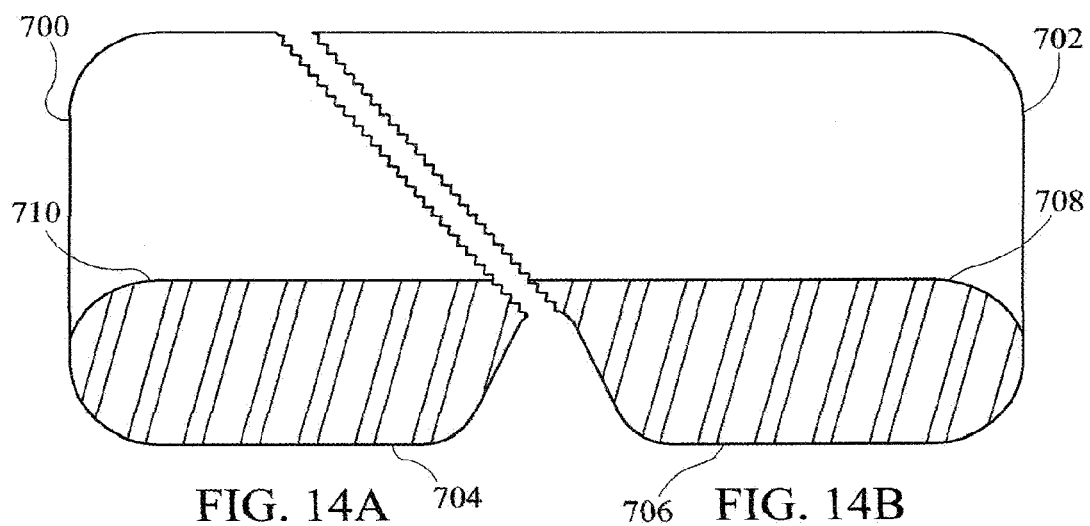
FIGS. 14a and 14b are views of FIG. 12 when the tablet has been broken at an angle from vertical.

Breaking the tablet of FIG. 13 may give two tablettes as shown in FIGS. 14*a* and 14*b*, though no limitation as to the direction of tablet breaking is intended. Largely inactive segment 310 of FIG. 1 has been divided into two segments, 700 in the smaller tablette as shown in FIGS. 2*a* and 702 in the larger tablette of FIG. 2*b*. Even though breaking as demonstrated is far from vertical, it is clear that the amount of drug in new segments 314 and 315 created from segment 312 of FIG. 1 is similar. Two new segments, 706 in FIGS. 2*b* and 704 in FIG. 2*a*, are created by said creation of the two tablettes. New interfaces 708 and 710 lie at the regions at which segments 702 and 706, and 700 and 704, respectively, adjoin.

Figure 15:
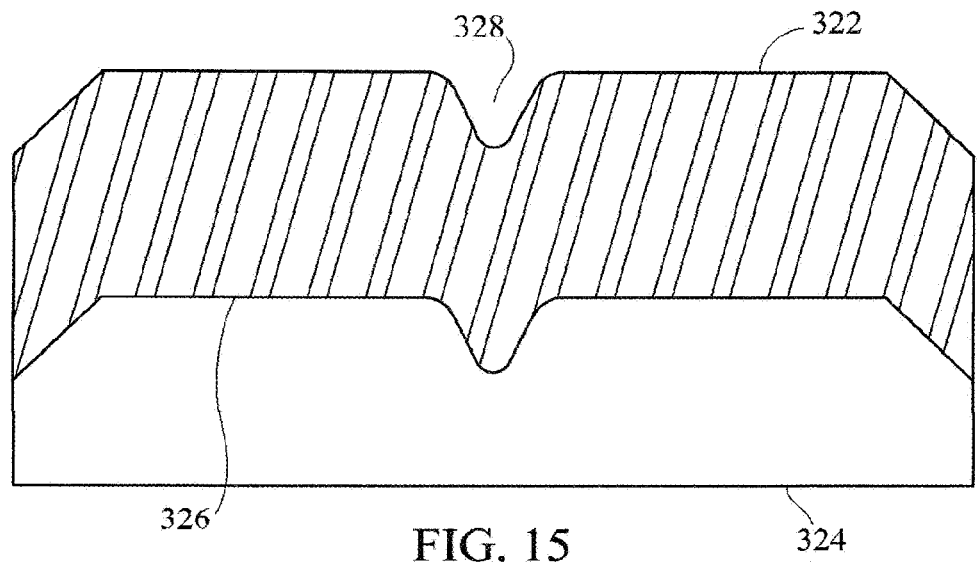
FIG. 15 is a cross-section of a tablet with two segments, one of which is substantially inactive.

FIG. 15 depicts a two-segment tablet. In this tablet, lower (bottom) segment 324 contains a drug different from that contained in upper (top) part 322. Score 328 indents segment 324. Interface 326 is present at the region at which segments 322 and 324 meet. The tablet of FIG. 8 is not a taller than wide tablet. FIG. 8 depicts a schematic of a tablet of the prior art of bilayer tablets. One may readily appreciate the difficulty inherent in attempting to break a tablet such as the tablet of FIG. 8 horizontally, through one segment only, or, analogously, a tablet similar to that of FIG. 8 but that in addition was provided with, say, a segment below that of segment 324.

Figure 16:
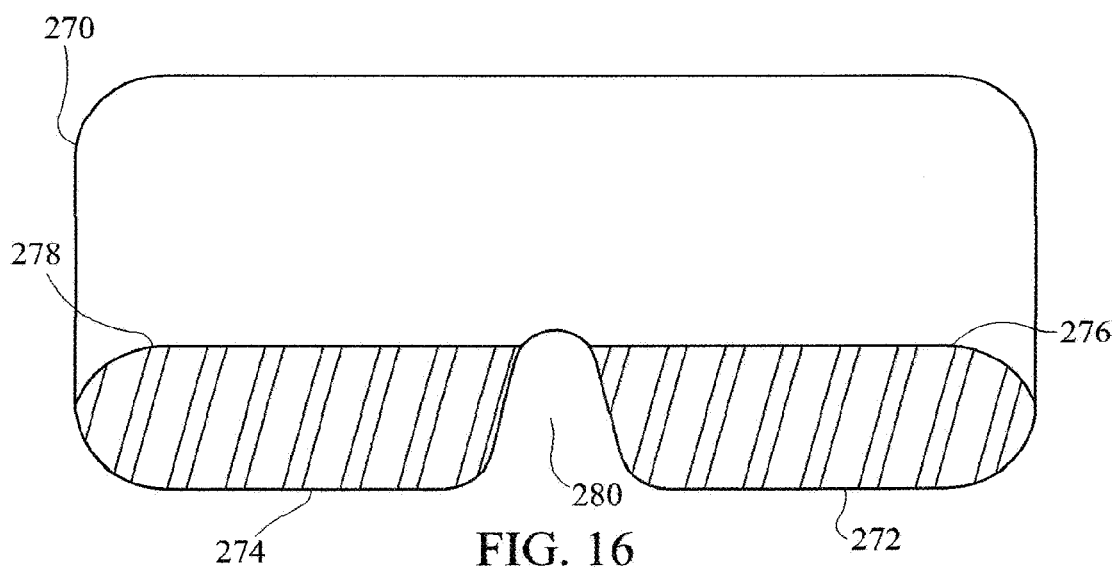
FIG. 16 is a cross-sectional view of a three segment tablet, two segments of which are unitary segments.

FIG. 16 depicts a tablet containing unitary segments 272 and 274 in vertical cross-section, front view. Both of said unitary segments adjoin the same face (surface) of segment 270, which is formed from a single granulation and due to mixing of granulations, contains a minimal amount of the drug that is present in segments 272 and 274. Interfaces 276 and 278 represent the regions at which segment 270 adjoins segments 272 and 274, respectively. Score 280 indents segment 270 and also represents the space between segments 272 and 274. Unitary segments 272 and 274 contain an altered release composition of a pharmaceutical. Segment 270 is formed from inactive excipients that do not affect the release rate of said pharmaceutical from the tablet.

Figures 17A, 17B:
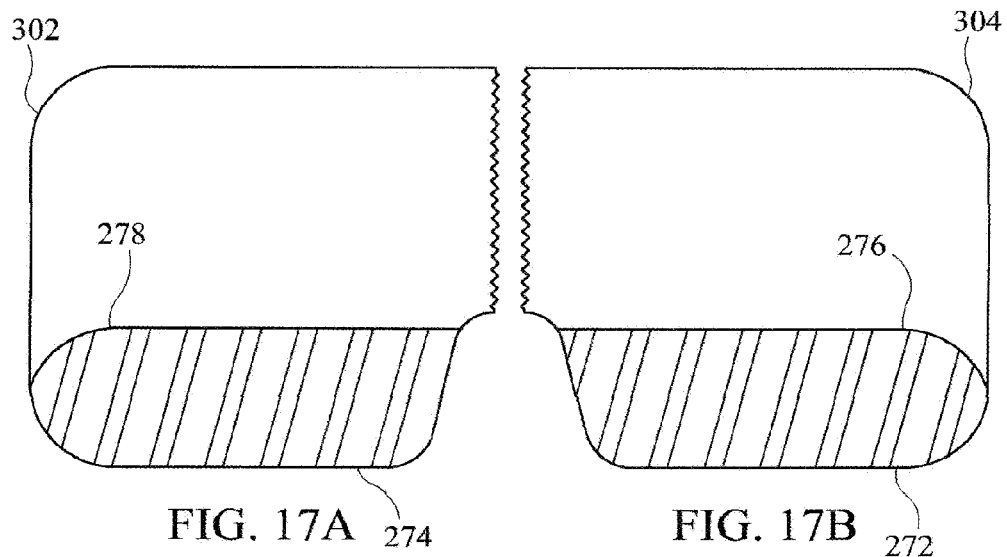
FIGS. 17a and 17b depict two tablettes formed by splitting the tablet of FIG. 16 through the top of the score.

FIGS. 17*a* and 17*b* depict the two tablettes created by breaking the tablet of FIG. 16 through segment 270. In FIG. 17*a*, segment 302 represents that part of segment 270 that adjoins intact segment 274. Interface 278 represents the region at which segments 302 and 274 meet. In FIG. 17*b*, interface 276 represents the region at which segments 304 and 272 meet. Score 280 and segment 270 of FIG. 16 are not considered to exist once the tablettes are formed. Each tablette of FIGS. 17*a* and 17*b* contains substantially equivalent mass assuming the score 280 of FIG. 16 is a bisecting score relative to the layer that became divided in the creation of segments 272 and 274.

Tablets of the nature of that of FIG. 16 may contain in the unitary segments a mixture of drugs or, as in FIG. 1, one drug. In addition, the granulation that forms segment 270 of FIG. 16 may be provided with a drug that is the same as, or different than, that of the divided layer. In such a case, it would be preferable that said drug provided in the upper layer (segment) would have a therapeutic effect and side effect profile that was not very sensitive to accuracy of subdivision of a dose.

In addition, no limitation exists as to the presence of one or more additional segments created superior to (i.e., above) segment 270, or the composition of such. Also, though less likely, there could be another set of different unitary segments inferior to (i.e., below) segments 272 and 274.

Figure 18:
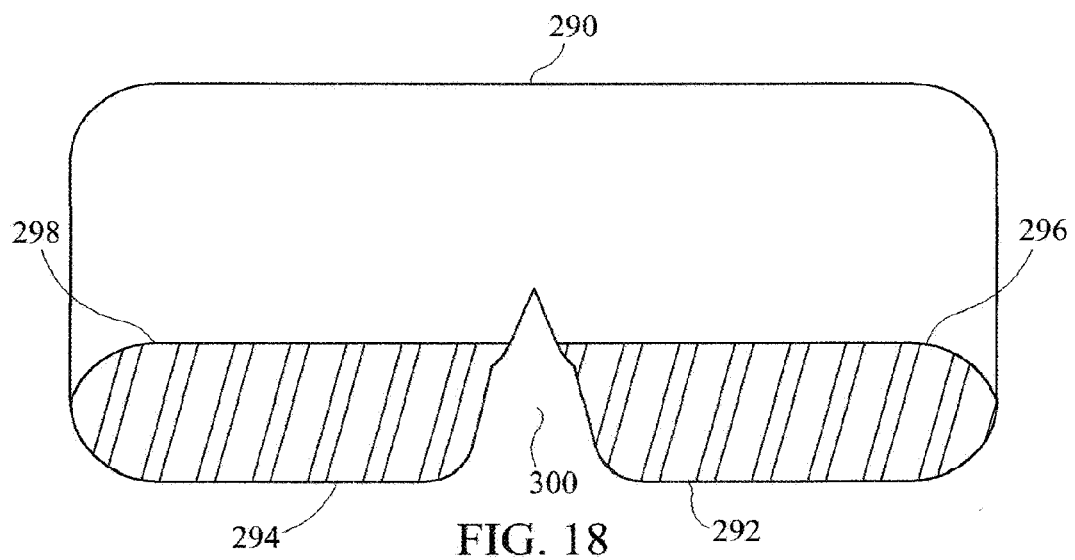
FIG. 18 is a cross-section view of a tablet with three segments, two of which are unitary segments.

FIG. 18 depicts a tablet in a cross-sectional view that is similar to that depicted in FIG. 13, but the tablet of FIG. 18 has a score 300 that extends more deeply into the non-unitary segment 290 than does score 280 of FIG. 13. A preferred method of producing score 300 is to use the embossing and manufacturing technique used for the tablet of FIG. 13 and then remove, such as with a file, material from segment 290. Alternatively, embossing of the appropriate size and shape may be able to be utilized to create score 300 directly. The tablet of FIG. 18 contains unitary segments 292 and 294. Interfaces 296 and 298 are present between segments 292 and 290, and 294 and 290, respectively.

Figure 19A:
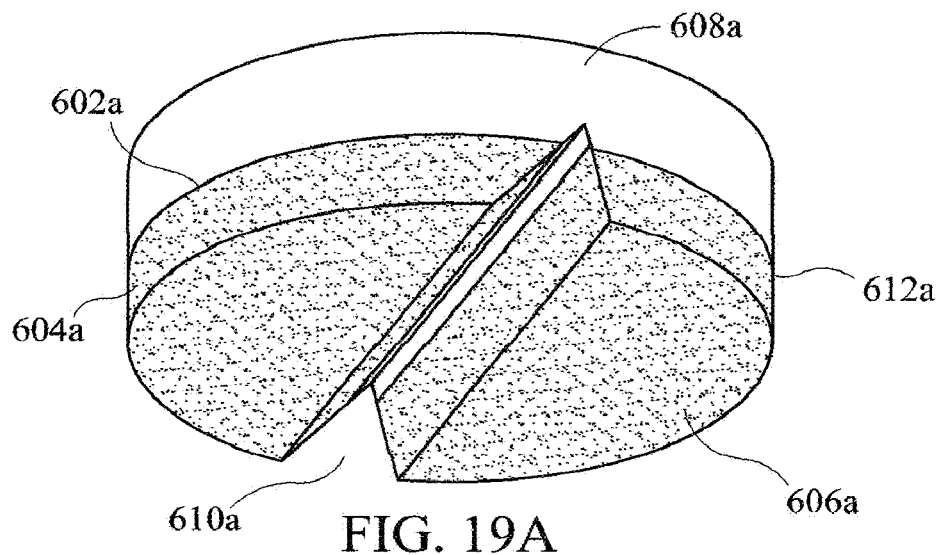
FIG. 19a is an external perspective view of a three segment tablet with two unitary segments.

FIG. 19*a* depicts an external view of a tablet containing unitary segments 604*a* and 606*a* that are at the bottom of the tablet. In this tablet, score 610*a* penetrates into clear, upper, non-unitary segment 608*a*. Interface 602*a* represents the region at which segment 608 meets segment 604*a*. Interface 612*a* represents the region at which segment 606*a* meets segment 608*a*.

Figure 19B:
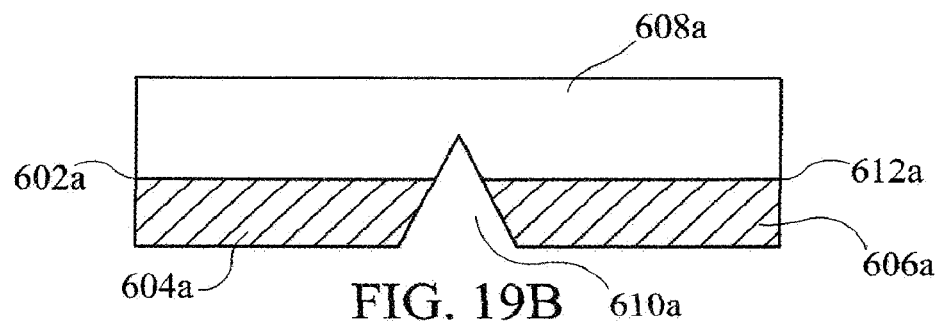

FIG. 19*b* depicts the same tablet depicted in FIG. 19*a*. This vertical cross-section is taken perpendicularly through score 610*a*, which occupies the diameter of the circular transverse cross-section of the tablet. The unitary segments of the tablets of FIGS. 19*a* and 19*b* comprises therapeutic quantities of diltiazem in beads producing controlled release of diltiazem to last twelve hours at least in therapeutic effect. Segment 608a has no therapeutically effective quantity of any drug.

Figure 20:
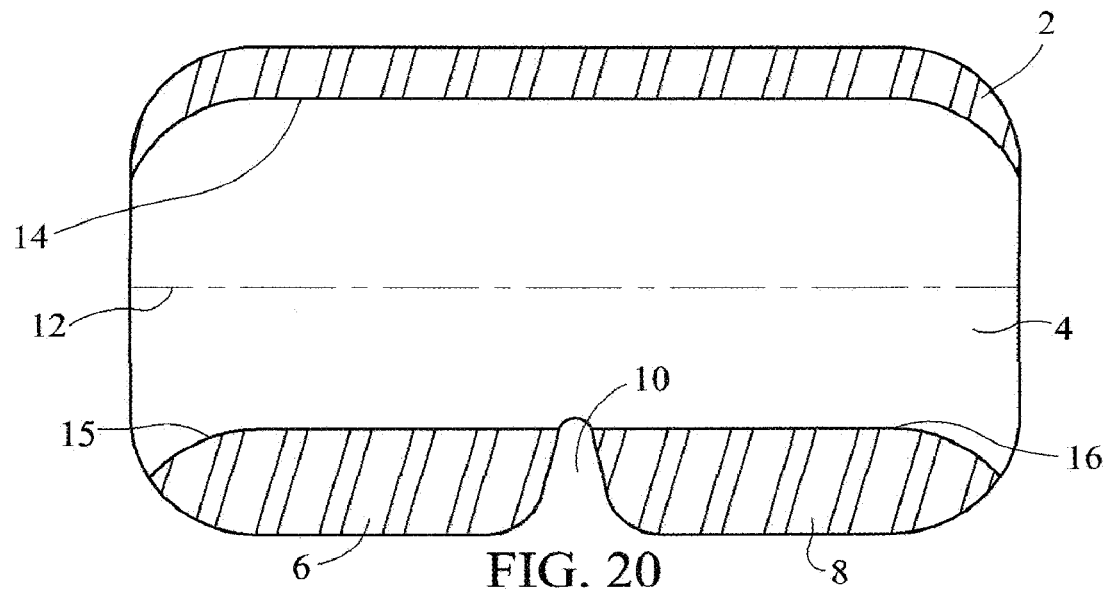
FIG. 20 shows a tablet with four segments, two of which are unitary segments.

FIG. 20 depicts a tablet containing four segments. Unitary segments 6 and 8, as with all unitary segments, are not contiguous with each other. Score 10 penetrates into segment 4. Segment 4 is a compound segment formed from substantially compositionally identical inactive granulations added sequentially with immediate release characteristics. Top segment 2 contains a therapeutic quantity of a drug that differs from the drug that is present in a therapeutic quantity in segments 6 and 8. Dotted line 12 reflects a surface score that runs transversely across segment 4. A preferred horizontal dimension for the tablet of FIG. 20 is 12-18 mm, but said dimension is not limited. Interface 14 depicts where segments 2 and 4 are contiguous. Interfaces 15 and 16 depict where segments 6 and 8, respectively, adjoin segment 4. Segment 4 contains therapeutically insignificant quantities of the drugs found in segments 6 and 2. The tablet of FIG. 20 may be broken usefully in two ways. One way is vertically through score 10 in the direction of segment 2; such breaking would not utilize the score reflected by dotted line 12, but would give a dose of half of the drug found in segments 6 and 8, though likely would not give a precise halving of the drug found in segment 2, due to difficulties with breaking scored tablets as was documented in the Background of the Invention, above. The result of another way of breaking said tablet is depicted schematically in FIGS. 21a and 21b.

The relative dimensions of segments in the tablet of FIG. 20 are not limited. In said tablet, an immediate release formulation of candesartan is present in the top segment, the middle segment lacks pharmacologic activity, and the unitary segments comprise sustained-release metoprolol.

Figure 21A:
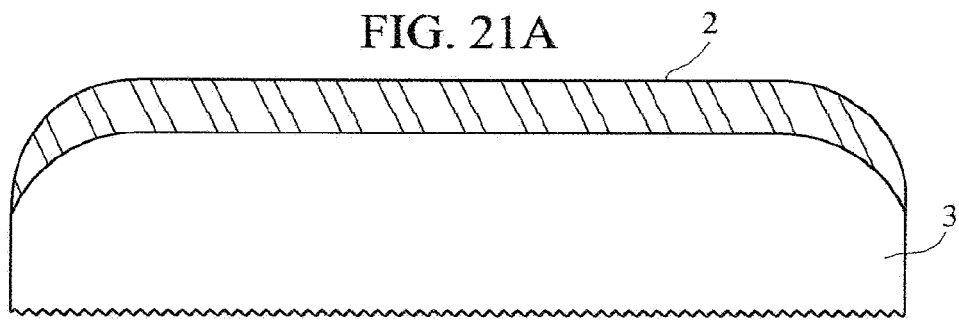
FIGS. 21a and 21b are cross-sections of each tablette formed by breaking the tablet of FIG. 20 through the middle segment.
Figure 21B:
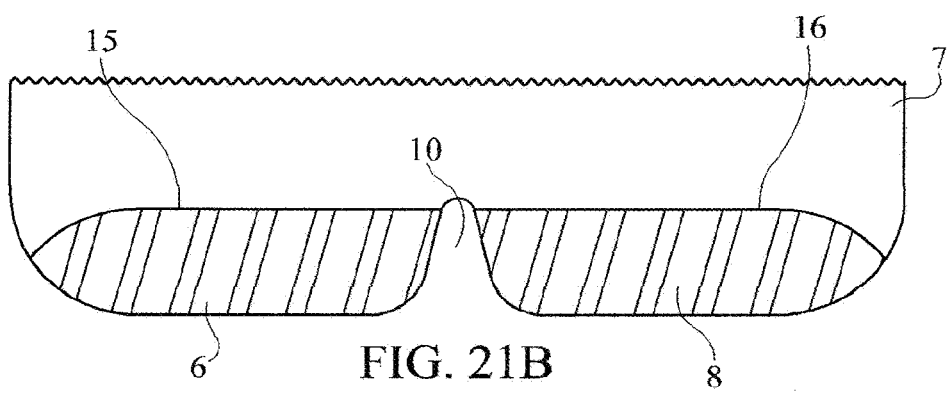

FIG. 21a shows a tablette formed from breaking the tablet of FIG. 5 through the horizontal score reflected by dotted line 12. As with other tablettes depicted herein, it is not assumed that breaking is even, but the tablettes are depicted so that breaking is contained substantially within segment 12, that is a segment interposed between upper segment 2 and lower segments 6 and 8 in the tablet of FIG. 5. The tablette of FIG. 21a demonstrates that segment 2 is intact, as is interface 14. Segment 3 is formed by the part of therapeutically inactive segment 4 of the tablet of FIG. 5 that remains contiguous with segment 2. The tablette of FIG. 21b depicts segments 6 and 8, and interfaces 15 and 16, as unchanged from the tablet of FIG. 5. Segment 7 is the part of segment 4 of FIG. 5 that becomes part of the tablette of FIG. 6b.

A wider than tall tablet with a relatively large inactive middle segment as depicted in FIG. 20 demonstrates that the invention of a tablet with a breakable inactive segment does not require that the tablet be taller than it is wide.

Figure 22A:
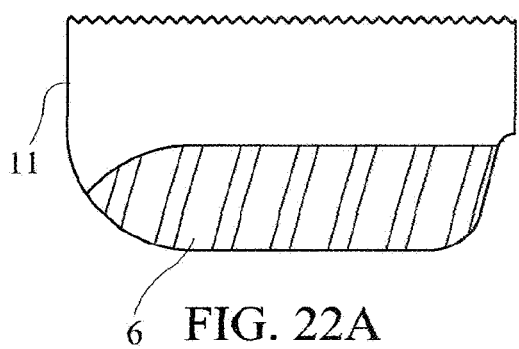
FIGS. 22a and 22b demonstrate the tablettes formed by breaking the tablette of FIG. 21b as guided by the score.
Figure 22B:
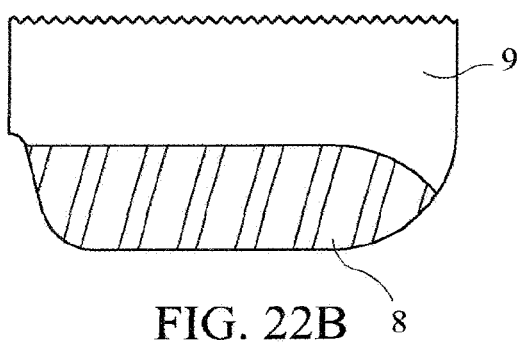

In addition, an external bottom view looking up at the unitary segments of FIG. 20 or FIG. 21b is not shown but if shown could demonstrate that the invention of unitary segments could easily allow for trisecting or quadrisecting FIGS. 22a and 22b demonstrate that second, or additional, tablettes can be formed by breaking a first tablette, e.g., tablettes of FIGS. 22a and 22b are formed by breaking of the tablette of FIG. 21b, as guided by a score.

FIGS. 23a-23h show schematic representations of embodiments of a capsule or sachet containing a dosage form, in accordance with the subject invention.

Figure 23A:
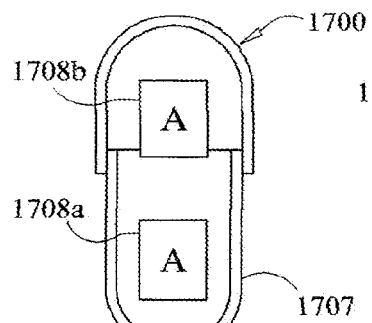

FIG. 23a shows a whole dosage form 1700 comprising a capsule 1707 containing identical pharmaceutical compositions A, represented as two separate dosage forms 1708a and 1708b. For example, composition A can represent an immediate release tablet or capsule having a drug or combination of drugs at a particular strength and in a particular formulation. The pharmaceutical composition can be segmented or non-segmented, e.g., a homogeneously blended composition contained within a capsule or compressed into a tablet form. The whole dosage form of this embodiment comprises two separate but identical compositions within a single capsule.

Figure 23B:
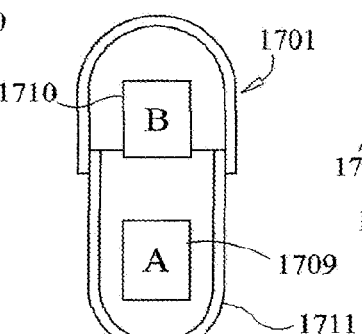
Figure 23C:
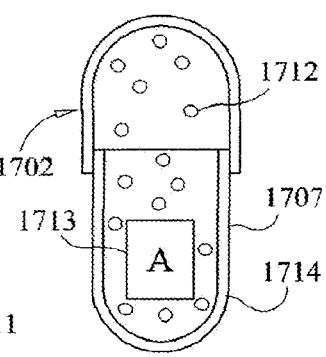

In FIG. 23b, the whole dosage form 1701 comprises two non-identical pharmaceutical compositions A and B contained within a capsule 1711. The separate non-identical pharmaceutical compositions, shown as 1709 and 1710 can be, for example, two completely different dosage forms having different drugs, different strengths, or different formulations. This represents embodiments that can include identical drugs provided at different strengths or formulated in different delivery systems, such as A being a drug in an immediate release formulation and B being the same drug in a controlled release formulation. As shown in FIG. 23c, the whole dosage form 1702 can comprise these different compositions A and B as different formulation types, such as a first drug formulated as a tablet 1713 and the same or different drug formulated as a powder or pellet composition 1712, and provided in a capsule 1714. Dosage form 1713 can be a segmented tablet in accordance with the subject invention or a capsule.

Figure 23D:
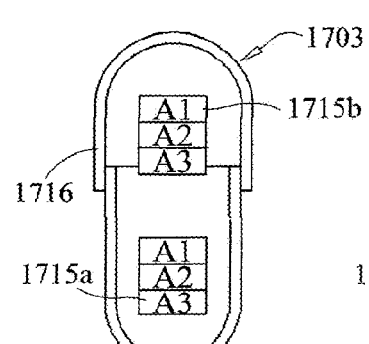
Figure 23E:
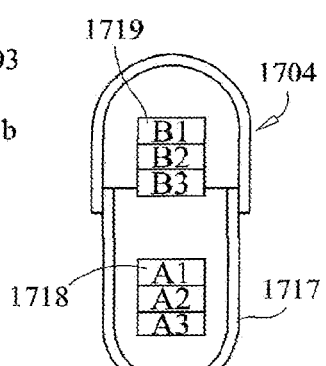
Figure 23F:
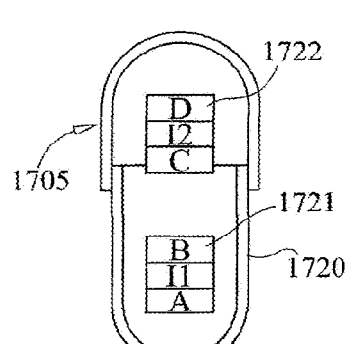
Figure 23G:
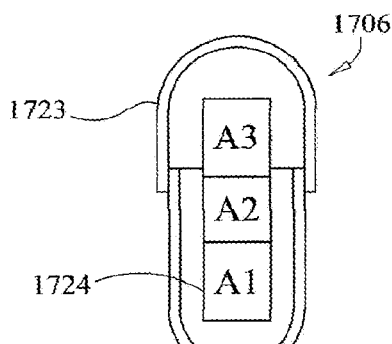

FIG. 23d shows a variation of an embodiment of FIG. 23a wherein the whole dosage form 1703 comprises two separate, identical dosage forms 1715a and 1715b contained within a capsule 716, wherein those identical dosage forms 1715a and 1715b are tablets or capsules further comprising segments A1, A2, and A3 which can comprise a drug A. Segments A1 and A3 can be the same or different but are different from A2, which is preferably substantially free of drug A and forms an inactive or relatively inactive segment interposed between segments A1 and A3. The segmented dosage forms allow for formation of tablettes by removal of the segmented dosage form from the capsule and dividing said segmented dosage form for administration of a partial dose from said segmented dosage form;

FIG. 23e represents a whole dosage form 1704 comprising a capsule 1717 containing two separate but non-identical segmented dosage forms 1718 and 1719 comprising, respectively, segments A1-A2-A3 and B1-B2-B3. Segments A1, A2 and A3 are as described above for FIG. 23d, and segments B1, B2, and B3 comprise drug or drug combination B different from A;

FIG. 23f represents a dosage form 1705 comprising a capsule 720 containing two separate but non-identical segmented dosage forms A-I1-B (1721) and C-I2-D (1722) wherein segments I1 represents an inactive or relatively inactive segment interposed between segments A and B, and segment I2 represents an inactive or relatively inactive segment interposed between segments C and D. Segments A, B, C and D represent a separate, but not necessarily different, drug, drug strength, or formulation in each represented segment;

FIG. 23g represents a whole dosage form 1706 comprising a capsule 1723 containing only one segmented dosage form 1724 which is composed of segments A1-A2-A3. Segments A1, A2, and A3 are as described for FIGS. 23d and 23e, and segment A2 is typically an inactive or relatively inactive segment interposed between two active segments which can be the same or different.

Figure 23H:
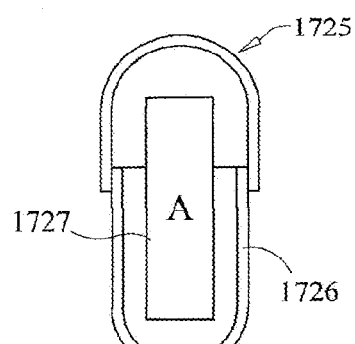

FIG. 23h shows a whole dosage form 1725 comprising a hollow capsule 1726 as an outer shell or housing which contains therewithin a single dosage form 1727 comprising a composition A. The composition A can include a drug or combination of drugs. The single dosage form can be a tablet, e.g., a homogeneous mixture of an active pharmaceutical ingredient and pharmaceutically acceptable excipients compressed into a tablet form, or can be another capsule which fits within the outer capsule.

Figure 24:
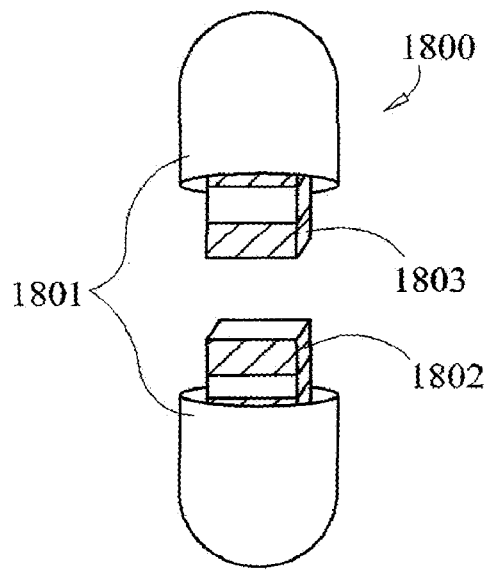
FIG. 24 shows a capsule of the subject invention opened to expose two dosage forms contained therein.
Figure 25A:
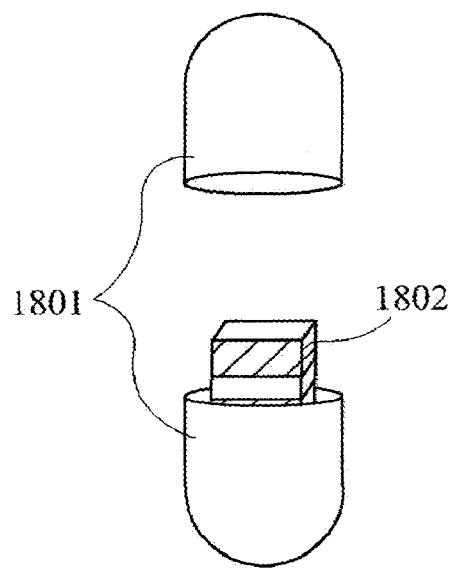
FIGS. 25a and 25b illustrate a capsule opened to expose a segmented tablet contained therein (FIG. 25a) and division of the segmented tablet to provide two tablettes either or both of which may be provided to a patient (FIG. 25b).
Figure 25B:
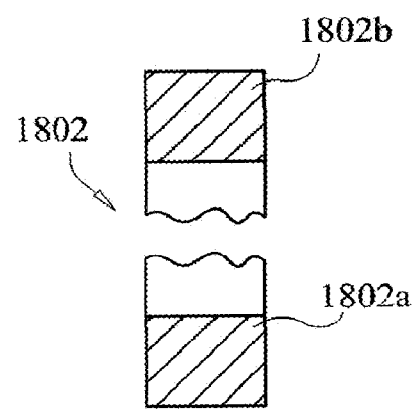

FIG. 24 shows a whole dosage form 1800 comprising a capsule 1801 opened to expose two separate segmented dosage forms 1802 and 1803 contained therein. As illustrated in FIGS. 25*a* and 25*b*, capsule 1801 of FIG. 24 can be opened to expose and separate the segmented tablet 1802 contained therein (FIG. 25*a*), whereby dividing segmented tablet 1802 can provide two tablettes 1802*a* and 1802*b* that can be administered to a patient (FIG. 25*b*).

The figures are not necessarily drawn to scale and are not intended to limit the size or shape of the dosage form or any subunit.

No limitation is intended regarding the number of subunits in the above or any of the instructive examples-provided. No limitation is intended as to the many examples of useful combinations of dosage subunits that may benefit from this invention. Numerous other mono-agents, in addition to those listed above may be formulated alone, or in combination with other drugs using the procedures of the invention.

It will be appreciated that no limitation is placed upon the nature, contents, active or inactive ingredients, or size or shape of either the subunits or the final dosage form, except that the final dosage form should be safe to use and is most preferably able to be taken into the body (e.g., ingested) by its intended user.

The scope and metes and bounds of the invention are defined by the appended claims.

The invention claimed is:

1. A dosage form comprising a capsule or sachet containing a divisible dose tablet, said tablet comprising a plurality of compressed segments, said tablet having a top and a bottom, and having a height that exceeds the width of said tablet, said height being measured vertically from the top to the bottom of said tablet while it is in a tablet die in which it is fully compressed, after said compression has been completed; and said width being measured as the greatest horizontal dimension of the tablet at a location halfway between said top and said bottom of said tablet, except that when the horizontal cross-section of said tablet is substantially rectangular, the width is defined by locating the two shorter sides of the perimeter of said horizontal cross-section, and measuring the length of a line that is at right angle to said shorter sides, said segments being compressed in a tablet die to form a taller-than-wide segmented tablet in said tablet die, wherein at least two segments are active segments comprising a composition containing one or more active pharmaceutical ingredient, and at least one of said plurality of compressed segments is an inactive segment located between said at least two active segments, said inactive segment forming a breaking region for dividing said tablet there through to provide at least two tablettes each comprising a compressed active segment and a portion of the compressed inactive segment.

2. The dosage form of claim 1 wherein said dosage form further comprises a non-tabletted composition within said capsule or sachet, said non-tabletted composition comprising a powder or pellet.

3. A method of treatment comprising the steps of:
 a. providing a dosage form of claim 1, and
 b. directing a patient or user of the dosage form to
  (i) remove the contained segmented composition from the capsule or sachet,
  (ii) divide said composition through the inactive segment to form a tablette containing a partial dose from the whole tablet, and
  (iii) administer at least one tablette to the patient or user.

4. The divisible tablet of claim 1 wherein said active segments comprising substantially identical drug or combination of drugs.

5. The divisible tablet of claim 1 comprising four or more segments.

6. The divisible tablet of claim 1 wherein each segment comprises a composition having immediate-release characteristics.

7. A method of treatment using a precise partial dose of a drug or drugs from a divisible whole tablet, said method comprising the steps of:
 (i) providing a divisible tablet of claim 1,
 (ii) breaking said tablet through an inactive segment, and
 (iii) administering a partial dose of a drug or drugs from the whole tablet.

8. A dosage form comprising a capsule or sachet containing a divisible dose compressed tablet having first and second active compressed segments comprising a composition containing a drug or combination of drugs, and a third inactive compressed segment between said active segments wherein said active segments are:
 formulated to have immediate-release characteristics,
 pharmaceutically compatible with one another, or
 substantially indentical compositions;
 said compressed tablet having a top and a bottom, and having a height that exceeds the width of said tablet, said height being measured vertically from the top to the bottom of said tablet while it is in a tablet die in which it is fully compressed, after said compression has been completed; and said width being measured as the greatest horizontal dimension of the tablet at a location halfway between said top and said bottom of said tablet, except that when the horizontal cross-section of said tablet is substantially rectangular, the width is defined by locating the two shorter sides of the perimeter of said horizontal cross-section, and measuring the length of a line that is at right angle to said shorter sides, said segments being compressed in a tablet die to form a taller-than-wide segmented tablet in said tablet die, wherein said third inactive segment forming a breaking region for dividing said tablet there through to provide at least two tablettes each comprising a compressed active segment and a portion of the compressed inactive segment.

\* \* \* \* \*